(12) United States Patent
Bai

(10) Patent No.: US 10,799,372 B2
(45) Date of Patent: Oct. 13, 2020

(54) PROSTHETIC FINGER

(71) Applicant: ZORPIA ROBOT CO. LTD, Rizhao, Shandong (CN)

(72) Inventor: Jinshi Bai, Rizhao (CN)

(73) Assignee: ZORPIA ROBOT CO. LTD, Rizhao (CN)

( * ) Notice: Subject to any disclaimer, the term of this patent is extended or adjusted under 35 U.S.C. 154(b) by 0 days.

(21) Appl. No.: 15/978,509

(22) Filed: May 14, 2018

(65) Prior Publication Data

US 2018/0256367 A1  Sep. 13, 2018

Related U.S. Application Data

(63) Continuation of application No. PCT/CN2016/110361, filed on Dec. 16, 2016.

(30) Foreign Application Priority Data

Nov. 18, 2015  (CN) .......................... 2015 1 0797183

(51) Int. Cl.
| A61F 2/58 | (2006.01) |
| A61F 2/54 | (2006.01) |
| A61F 2/70 | (2006.01) |
| A61F 2/68 | (2006.01) |
| A61F 2/50 | (2006.01) |

(52) U.S. Cl.
CPC ................ *A61F 2/586* (2013.01); *A61F 2/54* (2013.01); *A61F 2/68* (2013.01); *A61F 2/70* (2013.01); *A61F 2002/5072* (2013.01); *A61F 2002/6836* (2013.01)

(58) Field of Classification Search
CPC ...................................................... A61F 2/586
See application file for complete search history.

(56) References Cited

U.S. PATENT DOCUMENTS

| 5,116,386 A * | 5/1992 | Scribner ................. A61F 2/583 294/106 |
| 5,219,366 A * | 6/1993 | Scribner ................. A61F 2/583 294/103.1 |
| 9,486,925 B1 * | 11/2016 | Stroop ........................ B25J 1/04 |
| 2014/0107805 A1 * | 4/2014 | Varley ..................... A61F 2/586 623/24 |
| 2015/0230941 A1 * | 8/2015 | Jury ........................ A61F 2/583 623/64 |
| 2016/0089251 A1 * | 3/2016 | Mandl ..................... A61F 2/586 623/57 |
| 2016/0235555 A1 * | 8/2016 | Hunter .................... A61F 2/586 |
| 2018/0256367 A1 * | 9/2018 | Bai ......................... A61F 2/586 |
| 2018/0263791 A1 * | 9/2018 | Bai ......................... A61F 2/586 |
| 2019/0183661 A1 * | 6/2019 | Gill ........................ A61F 2/586 |

* cited by examiner

*Primary Examiner* — Jacqueline Woznicki
(74) *Attorney, Agent, or Firm* — Maschoff Brennan

(57) ABSTRACT

The present invention provides a prosthetic finger. The prosthetic finger includes a finger mounting rack, a worm gear, a rotating shaft, a base joint rack, a finger base knuckle, a finger proximal knuckle, a finger distal knuckle, a tension spring, and a transmission rope, a grommet, a motor reducer assembly, a first bevel gear, a worm, a second bevel gear. The prosthetic finger can ensure that the connection of all the parts is reliable, the rotation of the worm gear is smooth, the tension spring is protected, and the transmission rope is not easy to fall off, so that the working reliability of the whole prosthetic finger can be improved and the possibility of failure can be reduced on the whole.

6 Claims, 7 Drawing Sheets

PROSTHETIC FINGER

CROSS-REFERENCE TO RELATED APPLICATIONS

This application is a continuation of International Application No. PCT/CN2016/110361, filed on Dec. 16, 2016, which claims priority to Chinese Patent Application No. 201510797183.9, filed on Nov. 18, 2015, both of which are hereby incorporated by reference in their entireties.

TECHNICAL FIELD

The present invention relates to a bionic hand, in particular to a prosthetic hand which can be used for a disabled person, a finger of the prosthetic hand and part of a structure of the prosthetic hand.

BACKGROUND

A human hand generally has five fingers, namely a thumb, a forefinger, middle finger, a ring finger and a little finger respectively, in addition to the thumb having a special movement law, a movement law of other four fingers is basically the same. Each finger is divided into three knuckles, namely a base knuckle, a proximal knuckle and a distal knuckle respectively, which are connected by joints at corresponding positions, and a nail grows on the distal knuckle. For some disabled persons, a prosthetic hand is required to realize basic functions of a human hand.

Prior to 2007, the most popular prosthetic hand on the market was a single-degree-of-freedom prosthetic hand manufactured by OTTOBOCK company of Germany The prosthetic hand has only basic opening and closing functions, and a basic working principle of the prosthetic hand is that an electromyographic signal sensor senses a movement demand of a disabled person and sends a corresponding signal to a microcontroller, the microcontroller sends a control instruction to enable a micromotor to run, and the micromotor drives a prosthetic finger to move through a mechanical transmission chain, so as to realize the opening and closing of the prosthetic hand.

With the development of multi-finger dexterous hand technology in the robot field, the research of a multi-degree-of-freedom prosthetic hand has played a great promoting role. Since 2007, many kinds of multi-degree-of-freedom prosthetic hands have been developed, the vast majority of which employ an underactuated mechanism, i.e., generally only one micro-driving motor is required for one finger, while the movements of a base finger joint (corresponding to a connecting joint between the base knuckle and a palm) and a proximal finger joint (corresponding to a connecting joint between the proximal knuckle and the base knuckle) are coupled, with one micro-driving motor driving the base knuckle and the proximal knuckle simultaneously. The mechanical transmission of the base finger joint usually adopts cable (rope) transmission, bevel gear pair transmission, worm gear pair transmission or sliding screw pair transmission, etc., while the mechanical transmission of the proximal finger joint usually adopts cable (rope) transmission, connecting rod transmission or gear pair transmission, etc. Different combinations of a base finger joint transmission chain and a proximal finger joint transmission chain can form different products. At present, there are two kinds of prosthetic hands sold more in the market, one kind of prosthetic hand using worm gear pair transmission for a finger base finger joint and cable (rope) transmission for a proximal finger joint, and the other kind of prosthetic hand using sliding screw pair transmission for a finger base finger joint and connecting rod transmission for a proximal finger joint.

A prosthetic hand has more parts, the design of the prosthetic hand involves many problems, such as how to make these parts cooperate with one another to achieve basic functions similar to a human hand, how to ensure the reliability of work, how to reduce the complexity of a structure and the difficulty of assembly, how to reduce the cost, and how to make the structure beautiful, and these problems can be divided into many specific problems. Although productization of the prosthetic hand is realized at present, the prosthetic hand still has many defects in design, such as an existing iLim prosthetic hand has a finger DC motor with a lead connected to a lead output device of a base finger joint mounting rack, and the lead output device is provided with a fixing sleeve, a sliding guide pin and a compression spring. The structure of the prosthetic hand is complex, is difficult to miniaturize, and occupies a design space, and the structure and the appearance of a finger connector of the prosthetic hand are complex, including a conductive column which is in contact with a finger sliding guide pin, and a base joint outer cover which is complex in shape.

During the development of a prosthetic hand, the inventor finds at least the following problems in the prior art:

A prosthetic finger has more base finger joint parts and a complex assembly relationship, the parts are difficult to be effectively and accurately positioned, the assembly difficulty is high, especially base finger joint structures of some existing prosthetic fingers have simple assembly structures to result in poor work reliability of the base finger joint and easy failures.

For some existing prosthetic fingers, connecting structures between base knuckles and base joints are complex, and the finger base knuckles are difficult to be assembled to a base joint structure, and cannot be assembled simply and effectively.

For some existing prosthetic fingers using cable transmission for proximal finger joints, the proximal end of a transmission rope is connected to a worm gear, but a used specific connecting structure is not convenient for assembly, and the proximal end of the transmission rope is easy to fall off, which is not conducive to the reliable use of a prosthetic hand.

For some existing prosthetic fingers, the proximal finger joints use cable transmission, frequent bending and unbending of fingers can easily make a transmission rope rub and scratch on base knuckles of the fingers, long-term use of the prosthetic fingers easily makes the transmission rope be worn and even fractured to affect the service life of a cable transmission mechanism.

For some existing prosthetic fingers, tension springs are used for connecting proximal knuckles and base knuckles of the fingers to realize automatic reset of the proximal knuckles of the fingers during unbending of the fingers, while ends of the tension springs are fixedly connected, so the tension springs are frequently under the combined action of tension and bending moment, and long-term use of the fingers will make the tension springs have bending residual deformation. Therefore, the prosthetic fingers will have bending and unbending of fingers not in place, and the use characteristics of the prosthetic fingers and prosthetic hands are reduced.

For some existing prosthetic fingers, distal knuckles and proximal knuckles of the fingers are not distinguished structurally, so that the proximal knuckles of the fingers cannot be assembled with other parts conveniently, or end face lamination is used for the proximal knuckles and the distal knuckles of the fingers, and then a connection mode with other connecting pieces for connection is used, so that the connection reliability is poor, the structure is not beautiful enough.

For an existing prosthetic finger, because of part of the structure thereof has the above problems, the whole prosthetic finger has poor work reliability, and is not easy to assemble.

Since the amount of movement of the proximal knuckle of a thumb a human is very small, the design of a prosthetic thumb may not take this movement into account. However, for some existing prosthetic thumbs, the structure between the proximal knuckle of the thumb and the base knuckle of the thumb is very different from the connecting structure between the proximal knuckle and the distal knuckle of a general prosthetic finger (not thumb), so that special design and manufacture of the structure of the thumb is needed, or special design and manufacture of structures of the proximal knuckle of the thumb and the base knuckle of the thumb; and the difference between the prosthetic thumb and the general prosthetic finger can cause additional workload and processing cost, and the universality of parts is poor, which is not beneficial to reducing the cost.

The thumb has two postures, namely an opposite palm posture and a side palm posture, therefore, a prosthetic thumb needs to make posture rotary motion; however, for a mounting structure used by the existing prosthetic thumb, a lead for connecting a motor is introduced out from a side surface, so that when the prosthetic thumb converts the side palm and opposite palm postures, the lead is pulled, long-term use will cause the lead to be fractured, and in fact, the lead fracture of this kind of prosthetic thumb is a permanent fault.

Because part of the structure of the existing prosthetic thumb has the above problems, the cost of the whole prosthetic finger is high, the prosthetic finger is prone to failure, and the work reliability is poor.

Mounting structures of general prosthetic fingers (the other four prosthetic fingers except the thumb) of some existing prosthetic hands are as follows: the general prosthetic fingers and a finger connector of the prosthetic hand are connected by using finger axial single screws, and when the general fingers unbend, the finger axial single screws and the fingers point to a same direction, so the connection is not reliable, and short-term use will cause loose connection.

Because part of the structure of the existing prosthetic hand has the problems mentioned above, the reliability of the prosthetic hand is poor, and the cost is high.

SUMMARY

The present disclosure provides a more reliable prosthetic finger. The present invention provides a prosthetic finger including a finger mounting rack, a worm gear, a rotating shaft, a base joint rack, a finger base knuckle, a finger proximal knuckle, a finger distal knuckle, a tension spring, and a transmission rope; the worm gear is fixed on the finger mounting rack, a round hole with gap is provided on the worm gear, and a grommet is mounted in the round hole with gap, wherein the hole edge of the round hole with the gap is clamped at the diameter reduced part of the grommet; a motor reducer assembly is fixed in a base joint rack, a first bevel gear is fixed on an output shaft journal of the motor reducer assembly, a worm is mounted in the base joint rack through an elastic collar for hole and two sliding bearings, a second bevel gear is fixed on an input shaft journal of the worm, the second bevel gear is engaged with the first bevel gear, the base joint rack is provided with an open slot, the worm gear is positioned in the open slot and engaged with the worm, and a rotating shaft is penetrated on the base joint rack and the worm gear; the finger base knuckle has a cavity for accommodating the motor reducer assembly and is fixed on the base joint rack, the transmission rope runs through the inner space of the finger base knuckle, and the proximal end of the transmission rope is connected to the grommet; the finger proximal knuckle is rotatably connected to the distal end of the finger base knuckle, and two ends of the tension spring are rotatably connected to the finger base knuckle and the finger proximal knuckle respectively; and the finger proximal knuckle comprises a raised head part, a transmission rope connecting column is integrally arranged at a distal end of the raised head part, the distal end of the transmission rope is connected to the transmission rope connecting column, and a sleeving part is arranged on the finger distal knuckle and sleeved on the raised head part, and a part of the transmission rope is sandwiched between the sleeving part and the raised head part.

The prosthetic finger includes a finger mounting rack, a worm gear, a rotating shaft, a base joint rack, a finger base knuckle, a finger proximal knuckle, a finger distal knuckle, a tension spring, and a transmission rope, a grommet, a motor reducer assembly, a first bevel gear, a worm, a second bevel gear. The design that the two ends of the tension spring are rotable, and the design of the sleeving between the finger distal knuckle and the finger proximal knuckle are combined to ensure that the connection of all the parts is reliable, the rotation of the worm gear is smooth, the tension spring is protected, and the transmission rope is not easy to fall off, so that the working reliability of the whole prosthetic finger can be improved and the possibility of failure can be reduced on the whole.

REFERENCE SIGNS OF THE DRAWINGS

Figure 1:
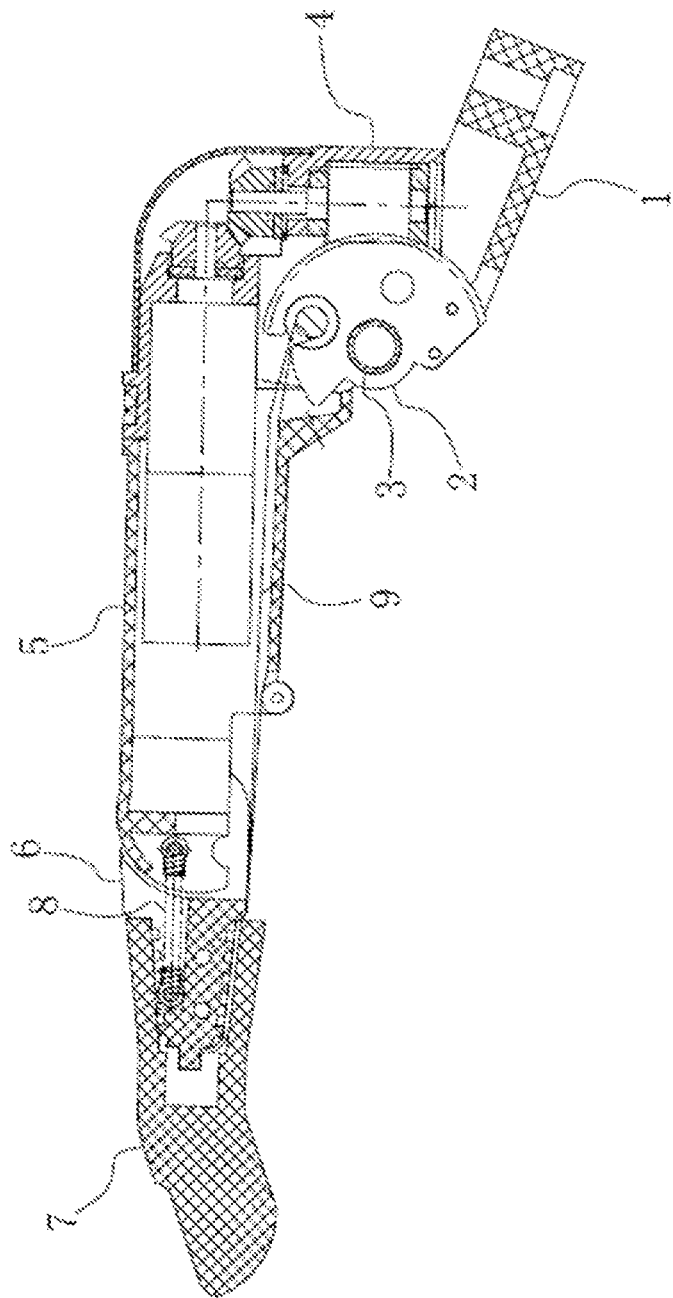
FIG. 1 is a schematic view of a structure of a prosthetic finger according to an embodiment of the present invention.
Figure 2:
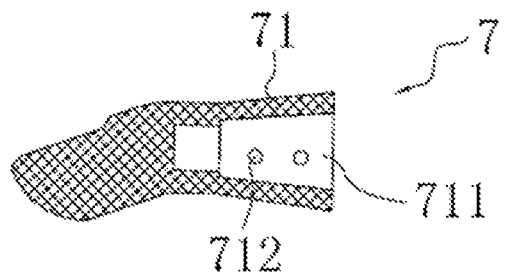
FIG. 2 is a schematic view of a section structure of a finger distal knuckle according to an embodiment of the present invention.
Figure 3:
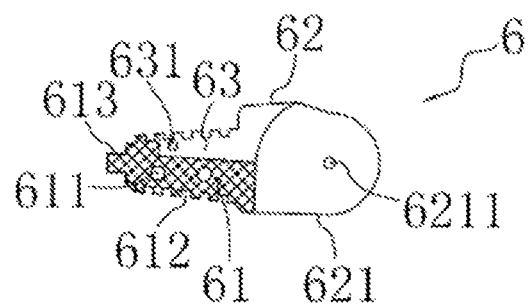
FIG. 3 is a schematic view of a section structure of a finger proximal knuckle according to an embodiment of the present invention.

1—finger mounting rack; 2—worm gear; 21—rotating shaft connecting part; 211—rotating shaft through hole; 22—rope pulling part; 23—engaging part; 24—worm gear fixing part; 241—worm gear fixing pin hole; 242—worm gear fixing pin; 25—round hole with gap; 251—grommet; 3—hollow shaft; 4—base joint rack; 41—motor reducer assembly mounting part; 411—motor reducer assembly mounting hole; 412—fan-shaped flange; 413—limiting flange; 42—worm mounting part; 421—worm main body accommodating cavity; 4211—elastic collar mounting groove; 422—sliding bearing mounting hole; 423—worm journal accommodating hole; 43—rotating shaft through connection part; 431—rotating shaft through connection concentric hole; 44—open slot; 401—motor reducer assembly; 4011—motor; 4012—reducer; 4013—mounting neck; 4014—output shaft journal; 402—first bevel gear; 403—second bevel gear; 404—worm; 4041—worm main body part; 4042—bearing mounting journal; 4043—input shaft journal; 405—first sliding bearing; 406—second sliding bearing; 407—elastic collar for hole; 408—finger tail cover; 5—finger base knuckle; 51—base knuckle main body; 511—slotted hole; 512—base knuckle screw mounting hole; 513—roller pin; 514—roller; 52—inter-wing connecting part; 521—base knuckle connecting wing, 5211—extension spring proximal end cylindrical pin mounting hole; 5212—arc-shaped cover plate; 6—finger proximal knuckle; 61—raised head part; 611—raised head part threaded hole; 612—raised head part annular groove; 613—transmission rope connecting column; 62—proximal knuckle main body; 621—proximal knuckle connecting wing; 6211—proximal knuckle connecting wing concentric hole; 63—tension spring accommodating groove; 631—extension spring distal end cylindrical pin mounting hole; 7—finger distal knuckle; 71—sleeving part; 711—sleeving cavity; 712—distal knuckle screw mounting hole; 72—distal knuckle mounting screw; 8—tension spring; 81—extension spring distal end cylindrical pin; 82—extension spring distal end cylindrical pin; 9—transmission rope; 1'—thumb mounting rack; 5'—thumb base knuckle; 51'—thumb base knuckle main body; 52'—thumb inter-wing connecting part; 521'—thumb base knuckle connecting wing; 6'—thumb proximal knuckle; 61'—thumb proximal knuckle raised head part; 62'—thumb proximal knuckle main body; 621'—thumb proximal knuckle connecting wing; 56'—thumb proximal finger joint locking pin; 7'—thumb distal knuckle; 71'—thumb distal knuckle sleeving part; 72'—thumb distal knuckle mounting screw; 10—thumb rotating rack; 101—thumb rotating rack open slot; 102—thumb mounting rack set screw; 11—thumb front support; 111—nut mounting hole; 112—thumb front supporting shaft nut; 12—thumb back support; 13—thumb front supporting shaft; 131—lead through hole; 14—thumb back supporting shaft; 15—prosthetic hand base plate; 151—finger base plate connecting screw; 16—finger connector; 161—tension nut; 162—finger connecting screw; 17—prosthetic hand dorsal shell; 171—general prosthetic finger base finger joint shield part; 18—wrist connecting piece.

DETAILED DESCRIPTION OF EMBODIMENTS

The structures of a prosthetic hand, a prosthetic finger and parts thereof in embodiments of the present invention will be described in detail below with reference to the accompanying drawings.

In order to facilitate an accurate understanding of the description of the present embodiment, the nouns of locality mentioned in the present embodiment are explained before the description is made: on the prosthetic finger and specific constituent parts, a "distal end" refers to an end near the fingertip of a finger, and a "proximal end" is opposite to the "distal end" and refers to an end near the root of the finger (or a finger base finger joint or palm); "upper" representing a position refers to a position on the finger corresponding to a position of the back of the hand when the finger unbends; "lower" representing a position refers to a position on the finger corresponding to the position of the palm of the hand; "side" representing a position refers to two other positions which are neither "upper" nor "lower", i.e., the positions of adjacent fingers; and an "adjacent finger side face" refers to a "side face", i.e., a side face on the finger facing an adjacent finger, which is neither "upper" nor "lower". The constituent parts of the prosthetic finger of the present embodiment will be described first, and then the entire prosthetic finger will be described.

1. A Base Finger Joint Structure of the Prosthetic Finger

The base finger joint of the prosthetic finger mainly performs functions similar to those of a base finger joint of a human hand, and the base knuckle of the human hand is used for connecting a finger base knuckle and a palm, so that the finger base knuckle and the palm are rotatably connected together. The base finger joint structure of the prosthetic finger according to the embodiment of the present invention can be specifically seen in FIG. 7 to FIG. 11 of the drawings in the specification. The base finger joint structure of the prosthetic finger provided by the embodiment of the present invention includes a base joint rack 4, a rotating shaft (hollow shaft 3 in the present embodiment) and a worm gear 2; a motor reducer assembly 401 is fixed in the base joint rack 4; a first bevel gear 402 is fixed on an output shaft journal 4014 of the motor reducer assembly 401; a worm 404 is mounted in the base joint rack 4 through an elastic collar for hole 407 and two sliding bearings; a second bevel gear 403 is fixed on an input shaft journal 4043 of the worm 404; the second bevel gear 403 is engaged with the first bevel gear 402; the base joint rack 4 is provided with an open slot 44 in which the worm gear 2 is positioned and is engaged with the worm 404, and a rotating shaft is passed through the base joint rack 4 and the worm gear 2.

The base finger joint structure of the prosthetic finger provided by the present embodiment can realize the functions similar to those of a finger base finger joint, the worm gear 2 is mounted through the open slot 44, the rotating shaft simultaneously passes through the base joint rack 4 and the worm gear 2, the open slot 44 can restrain the worm gear 2 to enable the worm gear to rotate stably, and the worm 404 is mounted through the elastic collar for hole 407 and the two sliding bearings to ensure that the worm 404 can rotate flexibly and be positioned reliably, so that the assembling difficulty is reduced, and the working reliability of the base finger joint structure can be improved.

Specifically, the base joint rack 4 includes a motor reducer assembly mounting part 41, a worm mounting part 42, and two rotating shaft through connection parts 43; the motor reducer assembly mounting part 41 and the worm mounting part 42 are connected into a whole through the two rotating shaft through connection parts 43, and an open slot 44 is formed between the two rotating shaft through connection parts 43; the motor reducer assembly 401 is fixed to the motor reducer assembly mounting part 41; the worm 404 is mounted in the worm mounting part 42; the worm gear 2 is provided with a rotating shaft through hole 211; the two rotating shaft through connection parts 43 are provided with rotating shaft through connection concentric holes 431 corresponding to the rotating shaft through hole 211; and the rotating shaft runs through the rotating shaft through hole 211 and the two rotating shaft through connection concentric holes 431.

Further, in order to fix the motor reducer assembly 401 to the motor reducer assembly mounting part 41, a motor reducer assembly mounting hole 411 is formed in the motor reducer assembly mounting part 41, the motor reducer assembly 401 includes a motor 4011, a reducer 4012 is connected to the motor 4011, a mounting neck 4013 is arranged on the reducer 4012, the diameter of the mounting neck 4013 is smaller than that of the reducer 4012, the output shaft journal 4014 extends out from the mounting neck 4013, and the mounting neck 4013 is fixed in the motor reducer assembly mounting hole 411. Here, the mounting neck 4013 of the motor reducer assembly 401 is used for fixing, and the structure of the motor reducer assembly mounting hole 411 is simple.

Further, in order to facilitate the mounting of the worm 404, a worm main body accommodating cavity 421, a sliding bearing mounting hole 422, and a worm journal accommodating hole 423 are sequentially formed in communication with one another in the worm mounting part 42; the diameter of the sliding bearing mounting hole 422 is smaller than that of the worm main body accommodating cavity 421, and the diameter of the worm journal accommodating hole 423 is smaller than that of the sliding bearing mounting hole 422; the end of the worm main body accommodating cavity 421 is opened, and an elastic collar mounting groove 4211 is circumferentially formed in the cavity wall of the worm main body accommodating cavity 421; the worm 404 includes a worm main body part 4041; the worm gear 2 is engaged with the worm main body part 4041; bearing mounting journals 4042 are integrally connected to two ends of the worm main body part 4041, and an input shaft journal 4043 is integrally connected to one of the bearing mounting journals 4042; the two sliding bearings are a first sliding bearing 405 and a second sliding bearing 406 respectively; the worm main body part 4041 is positioned in the worm main body accommodating cavity 421; the first sliding bearing 405 is positioned in the sliding bearing mounting hole 422; the second sliding bearing 406 is positioned in the worm main body accommodating cavity 421; the worm main body part 4041 is positioned between the first sliding bearing 405 and the second sliding bearing 406; the two bearing mounting journals 4042 are arranged in the first sliding bearing 405 and the second sliding bearing 406 respectively; the elastic collar mounting groove 4211 is provided with the elastic collar for hole 407; and the second sliding bearing 406 is positioned between the worm main body 4041 and the elastic collar for hole 407. The structure of each part of the worm gear and the worm gear mount part is finely designed (for example, various holes and grooves in the structure are used for realizing mounting and constraint positioning of the parts), so that the structure is simple, and is easy to assemble and reliable in work. Specifically, when assembling the worm 404, the first sliding bearing 405 may be first fitted into the sliding bearing mounting hole 422 from the open end of the worm main body accommodating cavity 421, the worm 404 is placed in, the second sliding bearing 406 is then arranged, and finally, the elastic collar for hole 407 is arranged to complete positioning and assembling of the worm 404.

Preferably, the rotating shaft in the present embodiment is the hollow shaft 3, and a finger tail cover 408 is connected to the base joint rack 4; the finger tail cover 408 covers the first bevel gear 402 and the second bevel gear 403; and the finger tail cover 408 has two insertion posts (not shown) which are inserted in two ends of the hollow shaft 3 respectively. Here, the finger tail cover 408 can shield connection positions of the two bevel gears, and the rotating shaft is a hollow shaft 3, so that on the one hand, the weight can be reduced while the structural strength is ensured, and on the other hand, the assembly of the finger tail cover 408 is assisted, and can be implemented by skillfully using the insertion posts on the finger tail cover 408.

Further, in the present embodiment, both the output shaft journal 4014 and the input shaft journal 4043 are journals with D-shaped cross sections, each of the first bevel gear 402 and the second bevel gear 403 has a D-shaped center hole, the D-shaped center hole of the first bevel gear 402 is sleeved on the journal with the D-shaped cross section of the output shaft journal 4014, and the D-shaped center hole of the second bevel gear 403 is sleeved on the input shaft journal 4043. The D-shaped center holes used here are matched with the journals with the D-shaped cross sections, and D-shaped cross section hole shaft constraint is adopted to realize the assembly of the bevel gears, so that the assembly difficulty is further simplified.

Preferably, the central axis of the output shaft journal 4014 in the present embodiment is orthogonal to the central axis of the input shaft journal 4043. Specifically, the central axis of the motor reducer assembly mounting hole 411 is orthogonal to the central axis of the sliding bearing mounting hole 422.

Specifically, in order to connect other parts, a finger base knuckle 5 is fixed on the base joint rack 4, and the worm gear 2 is fixed on the finger mounting rack 1.

Figure 4:
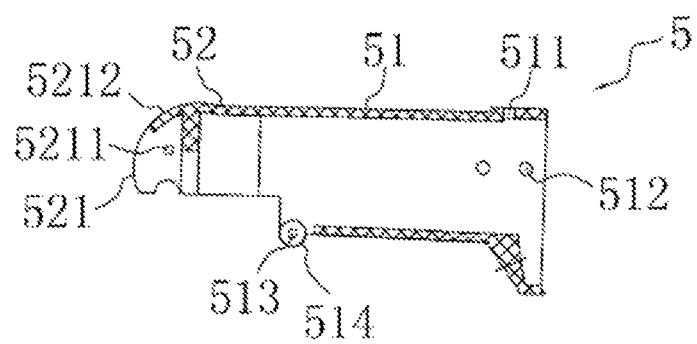
FIG. 4 is a schematic view of a section structure of a finger base knuckle according to an embodiment of the present invention.
Figure 5:
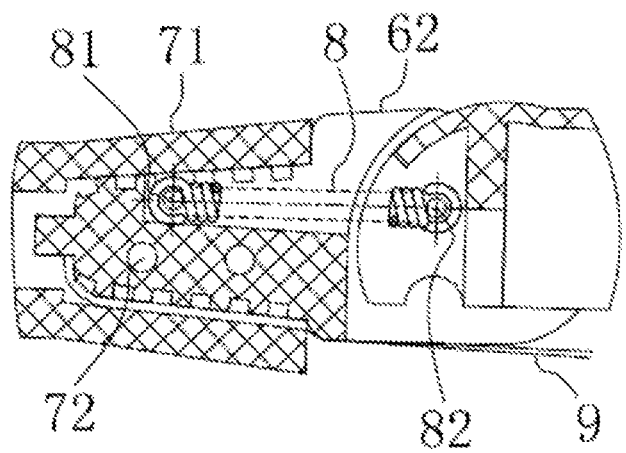
FIG. 5 is a partial enlarged drawing of the finger proximal knuckle in FIG. 1 and a near area of the finger proximal knuckle.
Figure 6:
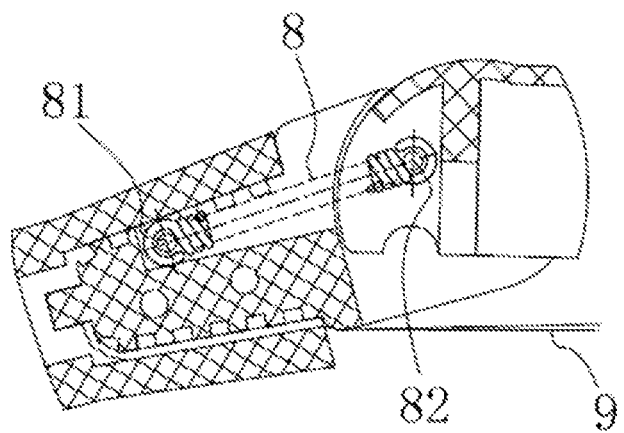
FIG. 6 is a partial enlarged drawing corresponding to FIG. 5 after the finger proximal knuckle is rotated relative to the finger base knuckle.
Figure 7:
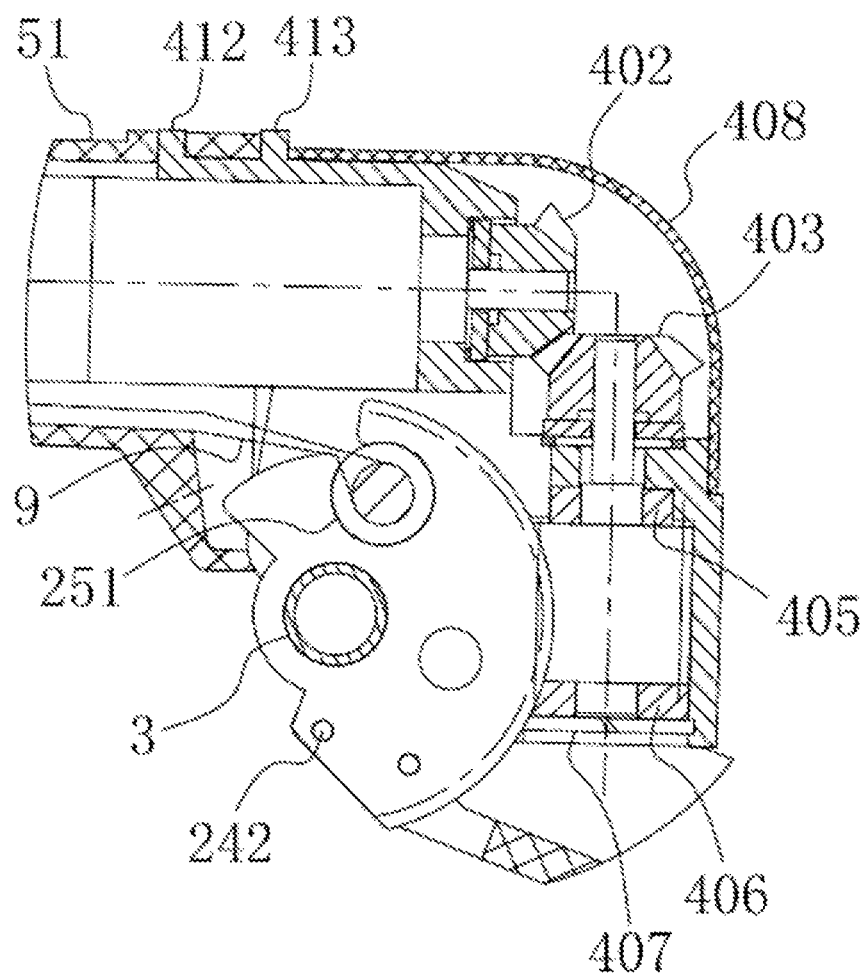
FIG. 7 is a partial enlarged drawing of a base joint rack in FIG. 1 and a near area of the base joint rack.
Figure 8:
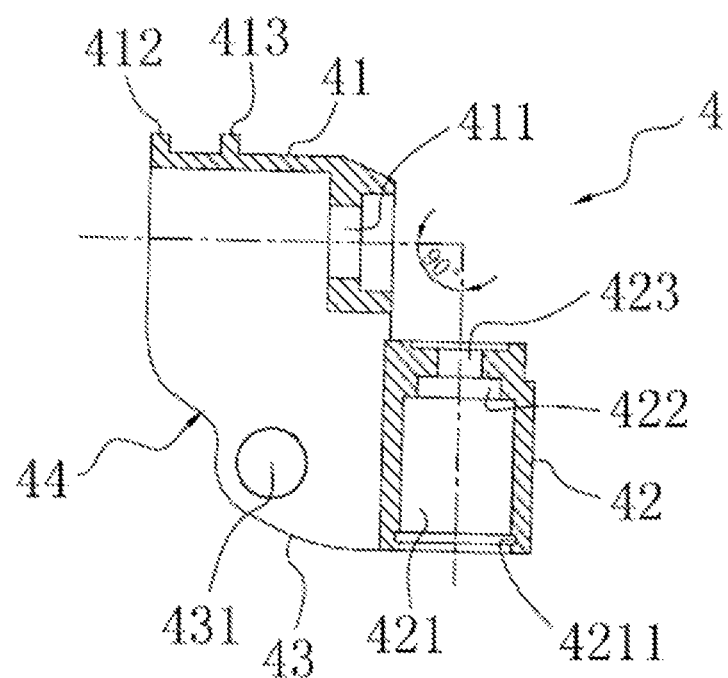
FIG. 8 is a schematic view of a section structure of the base joint rack according to an embodiment of the present invention.
Figure 9:
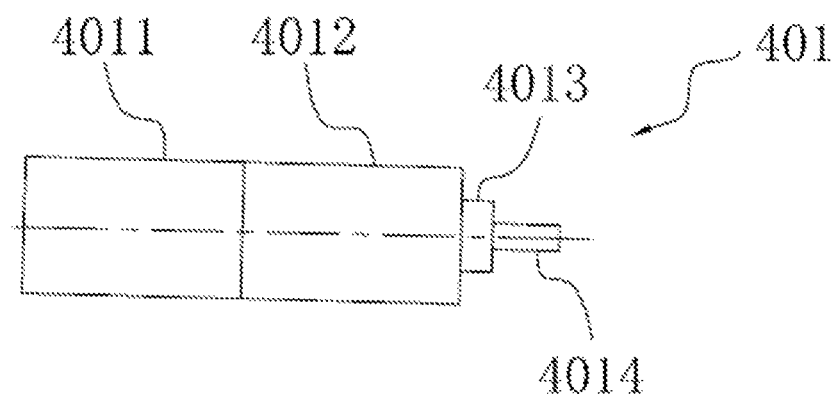
FIG. 9 is a schematic view of a structure of a motor reducer assembly according to an embodiment of the present invention.
Figure 10:
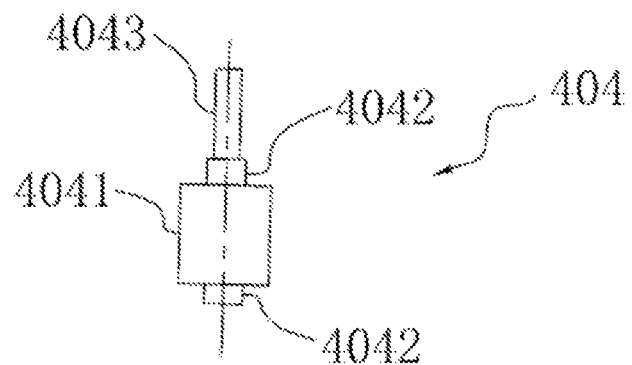
FIG. 10 is a schematic view of a structure of a worm according to an embodiment of the present invention.
Figure 11:
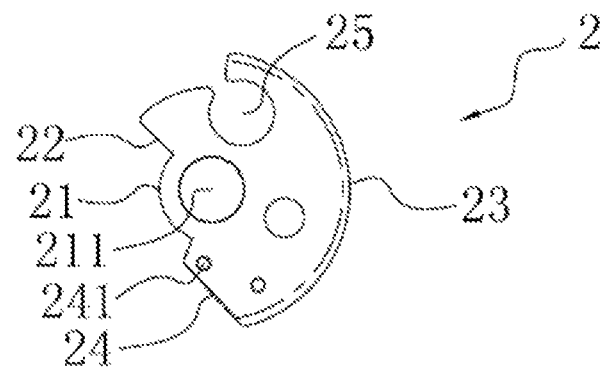
FIG. 11 is a schematic view of a structure of a worm gear according to an embodiment of the present invention.

2. A Connecting Structure Between a Base Knuckle and a Base Joint of the Prosthetic Finger The finger base knuckle 5 of the prosthetic finger needs to be fixed relative to the base joint rack 4. The connecting structure between the base knuckle and the base joint of the prosthetic finger according to the embodiment of the present invention can be specifically seen in FIGS. 4, 7 and 8 of the drawings in the specification. The connecting structure between the base knuckle and the base joint of the prosthetic finger provided by the embodiment of the present invention includes a base joint rack 4 and a finger base knuckle 5; the base joint rack 4 includes a motor reducer assembly mounting part 41; a motor reducer assembly mounting hole 411 is formed in the motor reducer assembly mounting part 41; a part of the motor reducer assembly 401 is fixed in the motor reducer assembly mounting hole 411; the finger base knuckle 5 includes a base knuckle main body 51; the base knuckle main body 51 is provided with a cavity for accommodating the motor reducer assembly 401; a fan-shaped flange 412 is arranged on the upper outer wall of the motor reducer assembly mounting part 41; a slotted hole 511 is formed in the base knuckle main body 51 corresponding to the fan-shaped flange 412; a part of the base knuckle main body 51 is sleeved with a part of the motor reducer assembly mounting part 41; and the fan-shaped flange 412 is positioned in the slotted hole 511.

The connecting structure between the base knuckle and the base joint of the prosthetic finger provided by the present embodiment is subjected to matching assembly in a sleeving manner by using the slotted hole 511 on the base knuckle main body 51 and the fan-shaped flange 412 on the motor reducer assembly mounting part 41 of the base joint rack 4, so that mutual positioning of the base knuckle and the base joint is easy to realize, and the assembly structure is simple.

Further, the motor reducer assembly mounting part 41 is provided with a base knuckle screw threaded hole (not shown), the axis of the base knuckle screw threaded hole is perpendicular to the axis of the motor reducer assembly 401, and a base knuckle screw mounting hole 512 corresponding to the base knuckle screw threaded hole is formed in the base knuckle main body 51; and a base knuckle set screw (not shown) is inserted into the base knuckle screw mounting hole 512, and is connected in the base knuckle screw threaded hole. Here, the base knuckle set screw is combined for further fixing, and constraint is performed from a plurality of different directions, so that the base knuckle main body 51 is not easily detached from the motor reducer assembly mounting part 41, and the fixing is more reliable.

Further, the head of the base knuckle set screw is positioned on an adjacent finger side face of the base knuckle main body 51. Here, the head of the base knuckle set screw is positioned on the adjacent finger side face of the finger, and due to a shielding effect of the adjacent finger (for example, when four fingers are unbent side by side), the base knuckle set screw can be hidden to a certain extent, so that the aesthetic property is enhanced. Preferably, the number of the base knuckle set screws in the present embodiment is two.

Further, a limiting flange 413 is arranged on the motor reducer assembly mounting part 41, and the proximal end of the base knuckle main body 51 abuts against the limiting flange 413. Here, the limiting flange 413 can play a role of auxiliary positioning to prevent axial displacement of the base knuckle main body 51.

3. A Connecting Structure Between the Worm Gear and the Transmission Rope of the Prosthetic Finger The proximal end of the transmission rope of the prosthetic finger which uses the worm gear and worm for the base finger joint movement and cable transmission for the proximal finger joint movement needs to be connected to the worm gear. The connecting structure between the worm gear and the transmission rope of the prosthetic finger according to the embodiment of the present invention can be specifically seen in FIGS. 7 and 11 in the drawings of the specification. The connecting structure between the worm gear and the transmission rope of the prosthetic finger, provided by the present embodiment, includes a transmission rope 9 and a worm gear 2; the worm gear 2 includes a rotating shaft connecting part 21; the rotating shaft connecting part 21 is integrally connected with a rope pulling part 22 for pulling the transmission rope 9, an engaging part 23 for engaging with the worm 404 and a worm gear fixing part 24 for fixedly connecting with the finger mounting rack 1; a round hole 25 with a gap is formed between the engaging part 23 and the rope pulling part 22; a grommet 251 is arranged in the round hole 25 with the gap; the proximal end of the transmission rope 9 is a double-line structure formed by doubling back a single line; the proximal end of the transmission rope 9 is sleeved at a diameter reduced part of the grommet 251; and the hole edge of the round hole 25 with the gap is clamped at the diameter reduced part of the grommet 251.

According to the connecting structure between the worm gear and the transmission rope of the prosthetic limb finger, provided by the present embodiment, the proximal end of the transmission rope 9 is connected with the grommet 251 through the round hole 25 with the gap, and the proximal end of the transmission rope 9 is a double-line structure formed by doubling back a single line, so that the connecting structure is simple to assemble, the transmission rope 9 is not easy to fall off, and the connection reliability is better.

Further, the round hole 25 with the gap is in rounded angle transition at the gap. The rounded angle transition is used here to avoid stabbing or cutting the transmission rope 9, so that the service life of the transmission rope 9 can be prolonged.

Further, the rotating shaft connecting part 21 is provided with a rotating shaft through hole 211, the edge of the rope pulling part 22 for contacting the transmission rope 9 is basically arc-shaped, and the arc-shaped arc line takes the center of the rotating shaft through hole 211 as the center of a circle. The edge of the rope pulling part 22 adopts an arc-shaped structure, and the arc-shaped arc line takes the center of the rotating shaft through hole 211 as the center of a circle, so that when the rope pulling part 22 pulls the transmission rope 9, the transmission rope 9 is pulled by butting against the arc-shaped edge, then a big contact surface between the transmission rope 9 and the rope pulling part 22 can be ensured, the stress on the proximal end of the transmission rope 9 can be more uniform, the transmission rope 9 can be protected, and the service life can be prolonged.

The worm gear 2 in the present embodiment is fixed to the finger mounting rack 1, specifically, a worm gear fixing pin hole 241 is formed in the worm gear fixing part 24, a worm gear fixing pin 242 is inserted in the worm gear fixing pin hole 241, and the worm gear fixing pin 242 is fixed to the finger mounting rack 1. Specifically, the present embodiment employs two worm gear fixing pins 242.

4. A Cable Transmission Structure of the Prosthetic Finger

During finger bending operation, the transmission rope in the cable transmission structure of the prosthetic finger pulls the proximal knuckle of the finger to rotate around a proximal finger joint. The transmission rope needs to be protected during finger bending and finger unbending. The cable transmission structure of the prosthetic finger in the present embodiment can be specifically seen in FIGS. 1 to 4 and FIG. 7 of the drawings of the specification. The cable transmission structure of the prosthetic finger provided by the present embodiment includes a transmission rope 9 and a finger base knuckle 5; the transmission rope 9 runs through the inner space of the finger base knuckle 5; the finger base knuckle 5 includes a base knuckle main body 51; the transmission rope 9 is positioned at the lower part in the base knuckle main body 51; a roller pin 513 is fixed at a position corresponding to the transmission rope 9 on the lower wall surface of the base knuckle main body 51; the axis of the roller pin 513 is perpendicular to the axis of the base knuckle main body 51; a roller 514 is sleeved on the roller pin 513; and a part of the roller 514 extends into a space in the wall surface of the base knuckle main body 51.

According to the cable transmission structure of the prosthetic finger provided by the present embodiment, the roller pin 513 and the roller 514 are mounted corresponding to the transmission rope 9 on the base knuckle main body 51 of the finger base knuckle 5, and a part of the roller 514 extends into the wall surface of the base knuckle main body 51; and when the proximal finger joint is bent or unbent, if the transmission rope 9 is pressed against the wall surface of the base knuckle main body 51, the transmission rope 9 will be pressed against the roller 514, so that friction and scraping caused by the finger base knuckle 5 on the transmission rope 9 can be reduced, the transmission rope 9 can be protected and the service life of the transmission rope 9 can be prolonged. Preferably, the transmission rope 9 in the present embodiment is a nylon rope. A high-strength nylon rope may be selected.

Specifically, a worm gear and a worm are used in the base finger joint movement in the present embodiment, so that the distal end of the transmission rope 9 is connected to the finger proximal knuckle 6, and the proximal end of the transmission rope 9 is connected to the worm gear 2.

In order to connect the distal end of the transmission rope 9 to the finger proximal knuckle 6, a transmission rope connecting column 613 is arranged at the distal end of the finger proximal knuckle 6, and the distal end of the transmission rope 9 is connected to the transmission rope connecting column 613. Here, the distal end of the transmission rope 9 can be conveniently connected by means of the transmission rope connecting column 613 at the distal end of the finger proximal knuckle 6. Further, the finger proximal knuckle 6 includes a raised head part 61 and a proximal knuckle main body 62 thicker than the raised head part 61, the transmission rope connecting column 613 is arranged at the distal end of the raised head part 61, a finger distal knuckle 7 is sleeved on the raised head part 61, a sleeving part 71 is arranged on the finger distal knuckle 7, is sleeved on the raised head part 61 and abuts against the proximal knuckle main body 62, and a part of the transmission rope 9 is sandwiched between the sleeving part 71 and the raised head part 61. Here, the sleeving part 71 also functions to tightly press the transmission rope 9 to further ensure that the distal end of the transmission rope 9 cannot fall off easily.

In order to connect the proximal end of the transmission rope 9 with the worm gear 2, the worm gear 2 includes a rotating shaft connecting part 21 to which a rope pulling part 22 for pulling the transmission rope 9, an engaging part 23 for engaging with the worm 404, and a worm gear fixing part 24 for fixedly connecting with the finger fixing rack 1 are integrally connected; a round hole 25 with a gap is formed between the engaging part 23 and the rope pulling part 22; a grommet 251 is mounted in the round hole 25 with the gap; the proximal end of the transmission rope 9 is a double-line structure formed by doubling back a single line; the proximal end of the transmission rope 9 is sleeved at a diameter reduced part of the grommet 251; and the hole edge of the round hole 25 with the gap is clamped at the diameter reduced part of the grommet 251. Here, the proximal end of the transmission rope 9 is connected to the grommet 251 by means of the round hole 25 with the gap, so that the transmission rope is assembled relatively simply, and is not easy to fall off.

5. A Connecting Structure Between the Proximal Knuckle and the Base Knuckle of the Prosthetic Finger In order to perform automatic reset during finger unbending, an elastic component is required to be adopted for connection between the finger proximal knuckle and the finger base knuckle of the prosthetic finger, and the use performance of this part of the structure is also required to be guaranteed. The connecting structure between the proximal knuckle and the base knuckle of the prosthetic finger in the present embodiment can be specifically seen in FIGS. 2 to 6 of the drawings in the specification. The connecting structure between the proximal knuckle and the base knuckle of the prosthetic finger provided by the present embodiment includes a finger base knuckle 5, a finger proximal knuckle 6 and a tension spring 8; the finger proximal knuckle 6 is rotatably connected to the finger base knuckle 5; an extension spring distal end cylindrical pin 81 is fixed on the finger proximal knuckle 6; an extension spring proximal end cylindrical pin 82 is fixed on the finger base knuckle 5; the axes of the extension spring distal end cylindrical pin 81 and the extension spring proximal end cylindrical pin 82 are parallel to the rotation axis of the finger base knuckle 5; and the two ends of the tension spring 8 are sleeved on the extension spring distal end cylindrical pin 81 and the extension spring proximal end cylindrical pin 82 respectively.

According to the connecting structure between the proximal knuckle and the base knuckle of the prosthetic finger provided by the present embodiment, the two ends of the tension spring 8 are no longer fixedly connected, but the extension spring distal end cylindrical pin 81 is fixed on the finger proximal knuckle 6, the extension spring proximal end cylindrical pin 82 is fixed on the finger base knuckle 5, and the two ends of the tension spring 8 are sleeved on the two cylindrical pins respectively, therefore, the distal end of the tension spring 8 can rotate around the extension spring distal end cylindrical pin 81 and the proximal end of the tension spring 8 can rotate around the extension spring proximal end cylindrical pin 82 due to the tensile force of the tension spring 8 when the finger proximal knuckle 6 rotates around the finger base knuckle 5, so that a bending moment effect on the tension spring 8 can be greatly reduced or even eliminated, the tension spring 8 will not generate bending residual deformation after being used for a long time, and then the use performance of prosthetic finger and prosthetic hand can be improved.

In order to rotatably connect the finger proximal knuckle 6 to the finger base knuckle 5, two proximal knuckle connecting wings 621 are arranged at the proximal end of the finger proximal knuckle 6, and proximal knuckle connecting wing concentric holes 6211 are correspondingly formed in the two proximal knuckle connecting wings 621; the finger base knuckle 5 includes a base knuckle main body 51, an inter-wing connecting part 52 is integrally connected at the distal end of the base knuckle main body 51, the width of the inter-wing connecting part 52 is smaller than that of the base knuckle main body 51, and the inter-wing connecting part 52 is positioned between the two proximal knuckle connecting wings 621; and convex hinged cylinders (not shown) are arranged on two side faces of the inter-wing connecting part 52, and the two proximal knuckle connecting wing concentric holes 6211 are sleeved on the two hinged cylinders respectively. The structures of the proximal knuckle connecting wings 621, the proximal knuckle connecting wing concentric holes 6211, the inter-wing connecting part 52 and the hinged cylinder are adopted to realize rotatable connection, so that the number of parts is reduced, and these structures can restrict the movement of the finger proximal knuckle 6 and the finger base knuckle 5 in other directions to ensure that the connection is more reliable and a rotation process is more stable.

In order to fix the tension spring proximal end cylindrical pin 82, two base knuckle connecting wings 521 are arranged at the distal end of the inter-wing connecting part 52, the proximal end of the tension spring 8 is positioned between the two base knuckle connecting wings 521, the base knuckle connecting wings 521 are provided with tension spring proximal end cylindrical pin mounting holes 5211, and the tension spring proximal end cylindrical pin 82 is inserted and fixed in the tension spring proximal end cylindrical pin mounting holes 5211.

In order to arrange the tension spring 8 and fix the tension spring distal end cylindrical pin 81, the finger proximal knuckle 6 is provided with a tension spring accommodating groove 63, and a tension spring distal end cylindrical pin mounting hole 631 is formed in the groove wall of the tension spring accommodating groove 63, and the tension spring distal end cylindrical pin 81 is inserted and fixed in the tension spring distal end cylindrical pin mounting hole 631.

In the present embodiment, the distal end edge of each base knuckle connecting wing 521 is an arc-shaped edge, the finger proximal knuckle 6 has an arc-shaped wall surface matched with the arc-shaped edge, an arc-shaped cover plate 5212 is commonly connected between the two base knuckle connecting wings 521, and the arc-shaped cover plate 5212 is arranged along the arc-shaped edge and is positioned above the proximal end of the tension spring 8. Here, the finger proximal knuckle 6 and the finger base knuckle 5 are in arc-shaped fit, and in conjunction with the design of the arc-shaped cover plate 5212, a gap above the proximal finger joint can be reduced, so that the effects of preventing entrance of objects and beautifying can be achieved to a certain extent.

6. A Connecting Structure Between the Distal Knuckle and the Proximal Knuckle of the Prosthetic Finger The connecting structure between the distal knuckle and the proximal knuckle of the prosthetic finger in the present embodiment can be specifically seen in FIGS. 2 to 6 of the drawings in the specification. The connecting structure between the distal knuckle and the proximal knuckle of the prosthetic finger provided by the present embodiment includes a finger proximal knuckle 6 and a finger distal knuckle 7; the finger proximal knuckle 6 includes a raised head part 61 and a proximal knuckle main body 62 thicker than the raised head part 61; a sleeving part 71 is arranged on the finger distal knuckle 7; a sleeving cavity 711 matched with the raised head part 61 is formed in the sleeving part 71; and the raised head part 61 is positioned in the sleeving cavity 711, and the sleeving part 71 is sleeved on the raised head part 61 and abuts against the proximal knuckle main body 62.

According to the connecting structure between the distal knuckle and the proximal knuckle of the prosthetic finger provided by the present embodiment, the structures of the raised head part 61, the proximal knuckle main body 62, the sleeving part 71 and the sleeving cavity 711 are connected with one another in a sleeving mode, so that an assembling space can be left for other parts, and the preassembly of the finger proximal knuckle 6 and other parts is facilitated; a plurality of contact points and contact surfaces can be arranged between the finger proximal knuckle 6 and the finger distal knuckle 7, so that the radial and axial positioning of the finger distal knuckle 6 can be simultaneously realized to a certain extent, the assembly between the finger proximal knuckle 6 and the finger distal knuckle 7 is facilitated, and the connection reliability is improved; in addition, the sleeving mode of the sleeving part 71 can enable the outer surface of the finger distal knuckle 6 to have a longer continuous surface, and an effect of improving the appearance of the finger can also be achieved. Preferably, the raised head part 61 is cone-shaped.

Further, a raised head part threaded hole 611 is formed in the raised head part 61, the axis of the raised head part threaded hole 611 is perpendicular to the axis of the raised head part 61, a distal knuckle screw mounting hole 712 is formed in the sleeving part 71 corresponding to the raised head part threaded hole 611, and the distal knuckle mounting screw 72 is inserted in the distal knuckle screw mounting hole 712 and connected to the raised head part threaded hole 611. Here, the distal knuckle mounting screw 72 is further used for fixing after sleeving, and the direction of the distal knuckle mounting screw 72 is perpendicular to the axial direction of the raised head part 61, so that not only the rotation of the sleeving part 71 but also the axial movement of the sleeving part 71 relative to the raised head part 61 can be restricted, the sleeving part 71 can be restricted in a plurality of directions, and the fixing between the finger proximal knuckle 6 and the finger distal knuckle 7 can be more reliable. Preferably, the number of distal knuckle mounting screws 72 is two.

Further, the head of the distal knuckle mounting screw 72 is positioned on an adjacent finger side face of the sleeving part 71. Here, the head of the distal knuckle mounting screw 72 is positioned on a side face of the finger, and the distal knuckle mounting screw 72 can be made hidden to some extent due to a shielding effect of adjacent fingers (for example, when four fingers are unbent side by side), thereby enhancing the aesthetic property. On the other hand, when the distal knuckle mounting screw 72 is in such a direction, other mechanisms (for example, a cable transmission mechanism and a spring reset mechanism) on the prosthetic finger may also be avoided. In the present embodiment, the arrangement of the distal knuckle mounting screw 72 keeps away from the transmission rope 9 and the tension spring 8.

In the present embodiment, the outer circumferential surface of the raised head part 61 is provided with a plurality of circles of raised head part annular grooves 612 along the circumferential direction, and due to the blocking of the plurality of circles of the raised head part annular groove 612, harmful substances such as grease, water and dust can be prevented from going deep into the prosthetic finger to a certain extent.

The movement of a proximal finger joint in the present embodiment adopts cable transmission, and in this case, in order to connect the transmission rope 9 to the finger proximal knuckle 6, a transmission rope connecting column 613 is integrally arranged at the distal end of the raised head part 61, one end of the transmission rope 9 is connected to the transmission rope connecting column 613, and a part of the transmission rope 9 is sandwiched between the sleeving part 71 and the raised head part 61. Thus, not only can the connection of the distal end of the transmission rope 9 be facilitated, but also the sleeving part 71 can act to tightly press the transmission rope 9, thereby ensuring that the distal end of the transmission rope 9 cannot fall off easily.

The proximal finger joint in the present embodiment relies on the tension of a spring to realize automatic reset when the finger unbends, and in view of this situation, in order to connect the tension spring 8 to the finger proximal knuckle 6, a tension spring accommodating groove 63 is formed in each of the raised head part 61 and the proximal knuckle main body 62, a tension spring distal end cylindrical pin mounting hole 631 is formed in the groove wall of the tension spring accommodating groove 63, a tension spring distal end cylindrical pin 81 is inserted and fixed in the tension spring distal end cylindrical pin mounting hole 631, and the distal end of the tension spring 8 is sleeved on the tension spring distal end cylindrical pin 81. Thus, not only can the assembly of the distal end of the tension spring 8 be facilitated, but also the distal end of the tension spring 8 can rotate around the tension spring distal end cylindrical pin 81 during rotation of the finger proximal knuckle 6, thereby reducing the bending residual deformation of the distal end of the tension spring 8 due to fixed connection and frequent bending moment actions.

7. A Prosthetic Finger

The prosthetic finger according to the present embodiment combines the structures of the previous parts, and can be specifically seen in FIGS. 1 to 11 of the drawings in the specification. The prosthetic finger provided by the embodiment of the present invention includes a finger mounting rack 1, a worm gear 2, a rotating shaft, a base joint rack 4, a finger base knuckle 5, a finger proximal knuckle 6, a finger distal knuckle 7, a tension spring 8 and a transmission rope 9; the worm gear 2 is fixed on the finger mounting rack 1, a round hole 25 with a gap is formed in the worm gear 2, a grommet 251 is arranged in the round hole 25 with the gap, and the hole edge of the round hole 25 with the gap is clamped at a diameter reduced part of the grommet 251; a motor reducer assembly 401 is fixed in a base joint rack 4, a first bevel gear 402 is fixed on an output shaft journal 4014 of the motor reducer assembly 401, a worm 404 is mounted in the base joint rack 4 through an elastic collar for hole 407 and two sliding bearings, a second bevel gear 403 is fixed on an input shaft journal 4043 of the worm 404, the second bevel gear 403 is engaged with the first bevel gear 402, the base joint rack 4 is provided with an open slot 44, the worm gear 2 is positioned in the open slot 44 and engaged with the worm 404, and a rotating shaft is penetrated on the base joint rack 4 and the worm gear 2; the finger base knuckle 5 has a cavity for accommodating the motor reducer assembly 401 and is fixed on the base joint rack 4, the transmission rope 9 runs through the inner space of the finger base knuckle 5, and the proximal end of the transmission rope 9 is connected to the grommet 251; the finger proximal knuckle 6 is rotatably connected to the distal end of the finger base knuckle 5, and two ends of the tension spring 8 are rotatably connected to the finger base knuckle 5 and the finger proximal knuckle 6 respectively; and the finger proximal knuckle 6 includes a raised head part 61, a transmission rope connecting column 613 is integrally arranged at a distal end of the raised head part 61, the distal end of the transmission rope 9 is connected to the transmission rope connecting column 613, and a sleeving part 71 is arranged on the finger distal knuckle 7 and sleeved on the raised head part 61, and a part of the transmission rope 9 is sandwiched between the sleeving part 71 and the raised head part 61.

According to the prosthetic finger provided by the present embodiment, the design of the grommet 251 in the worm gear 2, the design of the open slot 44 in the base joint rack 4, the design that the rotating shaft penetrates through a rotating shaft through hole 211 and two rotating shaft through connection concentric holes 431 at the same time, the design that the two ends of the tension spring 8 are rotable, and the design of the sleeving between the finger distal knuckle 7 and the finger proximal knuckle 6 are combined to ensure that the connection of all the parts is reliable, the rotation of the worm gear 2 is smooth, the tension spring 8 is protected, and the transmission rope 9 is not easy to fall off, so that the working reliability of the whole prosthetic finger can be improved and the possibility of failure can be reduced on the whole.

In order to facilitate the connection of the proximal end of the transmission rope 9, the proximal end of the transmission rope 9 is a double-line structure formed by doubling back a single line, and the proximal end of the transmission rope 9 is sleeved at a diameter reduced part of the grommet 251.

In order to shield the first bevel gear 402, the second bevel gear 403 and the space nearby the first bevel gear 402 and the second bevel gear 403, the rotating shaft is a hollow shaft 3, a finger tail cover 408 is connected to the base joint rack 4, and covers the first bevel gear 402 and the second bevel gear 403, and the finger tail cover 408 has two insertion posts which are inserted in the two ends of the hollow shaft 3 respectively.

In order to protect the part of the transmission rope 9 positioned in the finger base knuckle 5, the finger base knuckle 5 includes a base knuckle main body 51, the transmission rope 9 is positioned at the lower part in the base knuckle main body 51, a roller pin 513 is fixed at a position corresponding to the transmission rope 9 on the lower wall surface of the base knuckle main body 51, the axis of the roller pin 513 is perpendicular to the axis of the base knuckle main body 51, a roller 514 is sleeved on the roller pin 513, and a part of the roller 514 extends into a space inside the wall surface of the base knuckle main body 51.

In order to rotatably connect the two ends of the tension spring 8 to the finger proximal knuckle 5 and the finger proximal knuckle 6 respectively, a tension spring distal end cylindrical pin 81 is fixed on the finger proximal knuckle 6, a tension spring proximal end cylindrical pin 82 is fixed on the finger proximal knuckle 5, the axes of the tension spring distal end cylindrical pin 81 and the tension spring proximal end cylindrical pin 82 are parallel to the rotation axis of the finger proximal knuckle 5, and both ends of the tension spring 8 are sleeved on the tension spring distal end cylindrical pin 81 and the tension spring proximal end cylindrical pin 82 respectively.

In order to reliably connect the finger proximal knuckle 6 to the finger base knuckle 5, two proximal knuckle connecting wings 621 are arranged at the proximal end of the finger proximal knuckle 6, and proximal knuckle connecting wing concentric holes 6211 are correspondingly formed in the two proximal knuckle connecting wings 621; the finger base knuckle 5 includes a base knuckle main body 51, an inter-wing connecting part 52 is integrally connected at the distal end of the base knuckle main body 51, the width of the inter-wing connecting part 52 is smaller than that of the base knuckle main body 51, and the inter-wing connecting part 52 is positioned between the two proximal knuckle connecting wings 621; and convex hinged cylinders are arranged on two side faces of the inter-wing connecting part 52, and the two proximal knuckle connecting wing concentric holes 6211 are sleeved on the two hinged cylinders respectively.

In order to facilitate assembly positioning between the finger base knuckle 5 and the base joint rack 4, the finger base knuckle 5 includes a base knuckle main body 51 having a cavity for accommodating the motor reducer assembly 401, a fan-shaped flange 412 is arranged on an upper outer wall of the motor reducer assembly mounting part 41, a slotted hole 511 is formed in the base knuckle main body 51 corresponding to the fan-shaped flange 412, a part of the base knuckle main body 51 is sleeved with a part of the motor reducer assembly mounting part 41, and the fan-shaped flange 412 is positioned in the slotted hole 511.

In order to facilitate the assembly of the two bevel gears, both the output shaft journal 4014 and the input shaft journal 4043 are journals with D-shaped cross sections, each of the first bevel gear 402 and the second bevel gear 403 has a D-shaped center hole, the D-shaped center hole of the first bevel gear 402 is sleeved on the journal with the D-shaped cross section of the output shaft journal 4014, and the D-shaped center hole of the second bevel gear 403 is sleeved on the input shaft journal 4043.

In order to facilitate the assembly of parts in the base joint rack 4, the base joint rack 4 includes a motor reducer assembly mounting part 41, a worm mounting part 42, and two rotating shaft through connection parts 43; the motor reducer assembly mounting part 41 and the worm mounting part 42 are connected into a whole through the two rotating shaft through connection parts 43, and an open slot 44 is formed between the two rotating shaft through connection parts 43; the motor reducer assembly 401 is fixed to the motor reducer assembly mounting part 41; the worm 404 is mounted in the worm mounting part 42; the worm gear 2 is provided with a rotating shaft through hole 211; the two rotating shaft through connection parts 43 are provided with rotating shaft through connection concentric holes 431 corresponding to the rotating shaft through hole 211; and the rotating shaft runs through the rotating shaft through hole 211 and the two rotating shaft through connection concentric holes 431.

In order to facilitate the assembly of the motor reducer assembly 401 in the base joint rack 4, a motor reducer assembly mounting hole 411 is formed in the motor reducer assembly mounting part 41, the motor reducer assembly 401 includes a motor 4011, a reducer 4012 is connected to the motor 4011, a mounting neck 4013 is arranged on the reducer 4012, the diameter of the mounting neck 4013 is smaller than that of the reducer 4012, the output shaft journal 4014 extends out from the mounting neck 4013, and the mounting neck 4013 is fixed in the motor reducer assembly mounting hole 411.

In order to facilitate the assembly of the worm 404, a worm main body accommodating cavity 421, a sliding bearing mounting hole 422 and a worm journal accommodating hole 423 are sequentially formed in the worm mounting part 42 in communication with one another; the diameter of the sliding bearing mounting hole 422 is smaller than that of the worm main body accommodating cavity 421, and the diameter of the worm journal accommodating hole 423 is smaller than that of the sliding bearing mounting hole 422; the end of the worm main body accommodating cavity 421 is opened, and an elastic collar mounting groove 4211 is circumferentially formed in the cavity wall of the worm main body accommodating cavity 421; the worm 404 includes a worm main body part 4041, a bearing mounting journal 4042 is integrally connected to the two ends of the worm main body part 4041 respectively, and an input shaft journal 4043 is integrally connected to one of the bearing mounting journals 4042; the worm main body part 4041 is positioned in the worm main body accommodating cavity 421 and is engaged with an engaging part 23 of the worm gear 2; a first sliding bearing 405 is arranged in the sliding bearing mounting hole 422, and a second sliding bearing 406 is arranged in the worm main body accommodating cavity 421; the worm main body part 4041 is positioned between the first sliding bearing 405 and the second sliding bearing 406; one of the two bearing mounting journals 4042, which is connected to the input shaft journal 4043, is inserted in the first sliding bearing 405, and the other of the two bearing mounting journals 4042 is inserted in the second sliding bearing 406; an elastic collar for hole 407 is arranged in an elastic collar mounting groove 4211; and the second sliding bearing 406 is positioned between the worm main body part 4041 and the elastic collar for hole 407.

In order to protect the proximal end of the transmission rope 9, the edge of the worm gear 2 for contacting with the transmission rope 9 is basically arc-shaped, and the arc-shaped arc line takes the center of a rotating shaft through hole 211 as the center of a circle.

Compared with the prior art, the advantages of the prosthetic finger according to the present embodiment can also be seen in the previous description of the structures of the various parts. When the prosthetic finger in the present embodiment works, the motor reducer assembly 401 drives the first bevel gear 402 to rotate, the first bevel gear 402 drives the second bevel gear 403 and the worm 404 to rotate, the interaction between the worm 404 and the worm gear 2 causes the base joint rack 4 and the finger base knuckle 5 to rotate around the axis of the hollow shaft 3 during finger bending; under the acting force of the transmission rope 9, the finger proximal knuckle 6 and the finger distal knuckle 7 can bend relative to the finger base knuckle 5, and the tension spring 8 can be stretched; because the worm 404 and the worm gear 2 have a self-locking function, even if the power is cut off at this time, an object grasped by the prosthetic hand cannot easily fall off; during finger unbending, the motor reducer assembly 401 drives the first bevel gear 402 to rotate reversely, and the interaction between the worm 404 and the worm gear 2 causes the base joint rack 4 and the finger base knuckle 5 to rotate reversely around the axis of the hollow shaft 3; and under the acting force of the tension spring 8, the finger is reset and unbent.

8. A Connecting Structure Between a Proximal Knuckle and a Base Knuckle of a Prosthetic Thumb Through the design of the connecting structure between the proximal knuckle and the base knuckle of the prosthetic thumb, the connecting structure can be structurally universal with the structure of a general prosthetic finger (not the thumb). The connecting structure between the proximal knuckle and the base knuckle of the prosthetic thumb according to the embodiment of the present invention can be specifically seen in FIG. 12 of the drawings in the specification. The connecting structure between the proximal knuckle and the base knuckle of the prosthetic thumb, provided by the present embodiment, includes a thumb base knuckle 5' and a thumb proximal knuckle 6'; two thumb proximal knuckle connecting wings 621' are arranged at the proximal end of the thumb proximal knuckle 6', and thumb proximal knuckle connecting wing concentric holes (not shown) are correspondingly formed in the two thumb proximal knuckle connecting wings 621'; the thumb base knuckle 5' includes a thumb base knuckle main body 51', the distal end of the thumb base knuckle main body 51' is integrally connected with a thumb inter-wing connecting part 52', the width of the thumb inter-wing connecting part 52' is smaller than that of the thumb base knuckle main body 51'; the thumb inter-wing connecting part 52' is positioned between the two thumb proximal knuckle connecting wings 621'; raised hinged cylinders (not shown) are arranged on two side faces of the thumb inter-wing connecting part 52'; the thumb proximal knuckle connecting wing concentric holes are sleeved on the two hinged cylinders respectively; two thumb base knuckle connecting wings 521' are arranged at the distal end of the thumb inter-wing connecting part 52'; and a thumb proximal finger joint locking pin 56' is jointly inserted and fixed on the thumb base knuckle connecting wing 521' and the thumb proximal knuckle connecting wing 621'.

According to the connecting structure between the proximal knuckle and the base knuckle of the prosthetic thumb, provided by the embodiment, the adopted structures of the connecting wings and the hinged cylinders and the structure adopted by the proximal finger joint of a general prosthetic finger (not the thumb) have universality; according to the present embodiment, the thumb proximal finger joint locking pin 56' is jointly inserted and fixed on the thumb base knuckle connecting wing 521' and the thumb proximal knuckle connecting wing 621' to lock a proximal finger joint of the thumb to ensure that the thumb base knuckle 5' and the thumb proximal knuckle 6' are relatively fixed, so that the structure is simple, the structural complexity of the prosthetic hand can be reduced, and the universality of the parts can be improved, thereby reducing the cost.

Further, a sleeving structure in the prosthetic finger is also employed between the thumb proximal knuckle 6' and the thumb distal knuckle 7' of the prosthetic thumb; the thumb proximal knuckle 6' includes a thumb proximal knuckle raised head part 61' and a thumb proximal knuckle main body 62' thicker than the thumb proximal knuckle raised head part 61'; a thumb proximal knuckle connecting wing 621' is integrally connected to the proximal end of the thumb proximal knuckle main body 62'; and the thumb distal knuckle 7' is also included, and is provided a thumb distal knuckle sleeving part 71' which is sleeved on the thumb proximal knuckle raised head part 61' and butted against the thumb proximal knuckle main body 62'. The sleeving mode is convenient for secure and reliable assembly.

Further, a thumb proximal knuckle raised head part threaded hole (not shown) is formed in the thumb proximal knuckle raised head part 61', the axis of the thumb proximal knuckle raised head part threaded hole is perpendicular to the axis of the thumb proximal knuckle raised head part 61', a thumb distal knuckle screw mounting hole (not shown) is formed in the thumb distal knuckle sleeving part 71' corresponding to the thumb proximal knuckle raised head part threaded hole, and a thumb distal knuckle mounting screw 72' is inserted in the thumb distal knuckle screw mounting hole and connected to the thumb proximal knuckle raised head part threaded hole. Here, fixing is carried out in conjunction with the thumb distal knuckle mounting screw 72', and the thumb proximal knuckle 6' and the thumb distal knuckle 7' are not easily detached from each other. Preferably, the number of thumb distal knuckle mounting screws 72' is two.

Since the movement of the proximal knuckle of the thumb is locked, no transmission rope and tension spring are required. In the present embodiment, redundant tension spring accommodating grooves are formed in the thumb proximal knuckle raised head part 61' and the thumb proximal knuckle main body 62', and the tension spring is not connected to the thumb base knuckle 5' and the thumb proximal knuckle 6'.

9. A Mounting Structure for the Prosthetic Thumb

Figure 12:
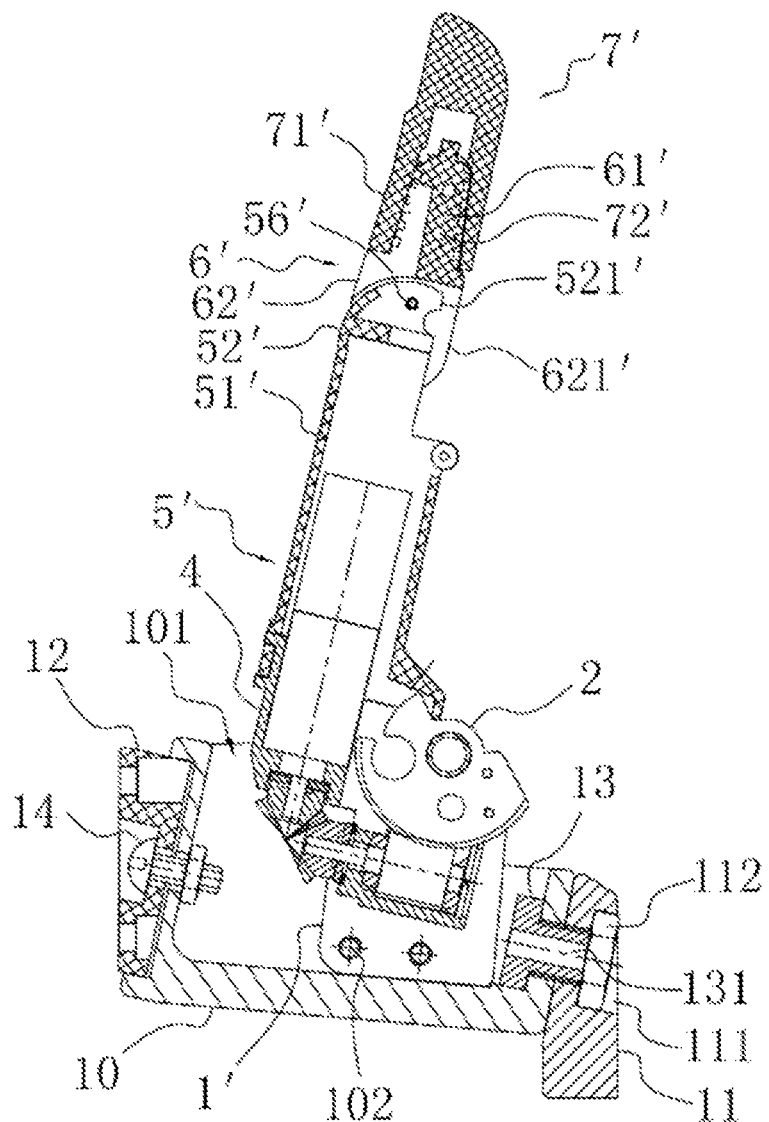
FIG. 12 is a schematic view of a structure of a prosthetic thumb according to an embodiment of the present invention.

The mounting structure for the prosthetic thumb according to the embodiment of the present invention can be specifically seen in FIG. 12 of the drawings in the specification. The mounting structure for the prosthetic thumb provided by the embodiment of the present invention includes a thumb mounting rack 1', a thumb rotating rack 10, a thumb front support 11 and a thumb back support 12; the thumb rotating rack 10 is provided with a thumb rotating rack open slot 101; the thumb mounting rack 1' is positioned in the thumb rotating rack open slot 101 and fixed on the thumb rotating rack 10; two ends of the thumb rotating rack 10 are coaxially connected with a thumb front supporting shaft 13 and a thumb back supporting shaft 14 respectively; the back end of the thumb front supporting shaft 13 is positioned in the thumb rotating rack open slot 101; the thumb front supporting shaft 13 is inserted in the thumb front support 11; the thumb back supporting shaft 14 is inserted in the thumb back support 12; a penetrating lead through hole 131 is formed in the thumb front supporting shaft 13 along the axial direction of the thumb front supporting shaft 13; and a lead (not shown) connected with a motor in the prosthetic thumb is inserted in the lead through hole 131 through the thumb rotating frame open slot 101.

The mounting structure for a prosthetic thumb, provided by the present embodiment, employs a specialized thumb rotating rack 10 for matched mounting of the prosthetic thumb. The thumb rotating rack 10 is connected between the thumb front support 11 and the thumb back support 12 through the coaxially arranged thumb front supporting shaft 13 and thumb back supporting shaft 14; and the lead connected with the motor in the prosthetic thumb passes through the lead through hole 131 through the thumb rotating rack open slot 101 and no longer passes through a side face as in the prior art, so that when the thumb rotating rack 10 is rotated due to opposite palm and side palm operation of the prosthetic thumb, the lead is not pulled and bent due to the rotation of the thumb rotating rack 10, and the service life of the lead is prolonged.

Specifically, in order to facilitate fixing the thumb mounting rack 1' to the thumb rotating rack 10, a thumb mounting rack fixing threaded hole (not shown) is formed in the thumb mounting rack 1', a thumb mounting rack set screw mounting hole (not shown) is formed in the thumb rotating rack 10 corresponding to the thumb mounting rack fixing threaded hole, and a thumb mounting rack set screw 102 is inserted in the thumb mounting rack set screw mounting hole and connected to the thumb mounting rack fixing threaded hole.

In order to facilitate assembly of the thumb front supporting shaft 13, the thumb front supporting shaft 13 includes a head part and a screw part (not shown), the lead through hole 131 runs through the head part and the screw part, a nut mounting hole 111 is formed in the thumb front support 11, a thumb front supporting shaft nut 112 is arranged in the nut mounting hole 111, and the screw part is inserted in the thumb rotating rack 10 and the thumb front support 11 and connected to the thumb front supporting shaft nut 112.

In order to facilitate the assembly of the thumb back supporting shaft 14, the thumb back supporting shaft 14 includes a thumb back supporting shaft bolt (not shown) and a thumb back supporting shaft nut (not shown), the thumb back supporting shaft nut is positioned in the thumb rotating rack open slot 101, and the thumb back supporting shaft bolt is inserted in the thumb back support 12 and the thumb rotating rack 10 and connected to the thumb back supporting shaft nut.

10. A Prosthetic Thumb

Part of the parts of the prosthetic thumb according to the embodiment of the present invention are commonly used with parts of a general prosthetic finger, but are distinguished on names with "thumb", so that some parts of the prosthetic thumb below are not labeled with drawing reference signs and the previous drawings can be used for reference during reading. The prosthetic thumb according to the embodiment of the present invention can be seen specifically in FIGS. 7 to 12 of the drawings in the specification. The prosthetic thumb provided by the embodiment of the present invention includes a thumb mounting rack 1', a thumb worm gear, a thumb rotating shaft, a thumb base joint rack, a thumb base knuckle 5', a thumb proximal knuckle 6', a thumb distal knuckle 7', a thumb rotating rack 10, a thumb front support 11 and a thumb back support 12; the thumb worm gear is fixed on the thumb mounting rack 1'; the thumb base joint rack is rotatably connected to the thumb worm gear through a thumb rotating shaft; the thumb base knuckle 5' is fixed on the thumb base joint rack; the thumb proximal knuckle 6' is fixed on the thumb base knuckle 5'; the thumb distal knuckle 7' is fixed on the thumb proximal knuckle 6'; a thumb motor reducer assembly, a thumb first bevel gear, a thumb second bevel gear and a thumb worm are arranged in the thumb base joint rack; the thumb motor reducer assembly can sequentially drive the thumb first bevel gear, the thumb second bevel gear and the thumb worm to rotate; the thumb worm gear is engaged with the thumb worm; the thumb rotating rack 10 is provided with a thumb rotating rack open slot 101; the thumb mounting rack 1' is positioned in the thumb rotating rack open slot 101 and fixed on the thumb rotating rack 10; the thumb front supporting shaft 13 and the thumb back supporting shaft 14 are coaxially connected at two ends of the thumb rotating rack 10 respectively; the back end of the thumb front supporting shaft 13 is positioned in the thumb rotating rack open slot 101; the thumb front supporting shaft 13 is inserted in the thumb front support 11; the thumb back supporting shaft 14 is inserted in the thumb back support 12; the thumb front supporting shaft 13 is internally provided with a penetrating lead through hole 131 along the axial direction of the thumb front supporting shaft 13; and a lead which is connected with a motor in the prosthetic thumb is inserted in the lead through hole 131 through the thumb rotating rack open slot 101.

The prosthetic thumb provided by the embodiment of the present invention employs a specialized thumb rotating rack 10 for matched mounting of the prosthetic thumb; the thumb rotating rack 10 is connected between the thumb front support 11 and the thumb back support 12 through the coaxially arranged thumb front supporting shaft 13 and thumb back supporting shaft 14; and the lead connected with the motor in the prosthetic thumb passes through the lead through hole 131 through the thumb rotating rack open slot 101 and no longer passes through a side face as in the prior art, so that when the thumb rotating rack 10 is rotated due to opposite palm and side palm operation of the prosthetic thumb, the lead is not pulled and bent due to the rotation of the thumb rotating rack 10, and the service life of the lead is prolonged.

Further, two thumb proximal knuckle connecting wings 621' are arranged at the proximal end of the thumb proximal knuckle 6', and thumb proximal knuckle connecting wing concentric holes are correspondingly formed in the two thumb proximal knuckle connecting wings 621'; the thumb base knuckle 5' includes a thumb base knuckle main body 51', the distal end of the thumb base knuckle main body 51' is integrally connected with a thumb inter-wing connecting part 52', the width of the thumb inter-wing connecting part 52' is smaller than that of the thumb base knuckle main body 51'; the thumb inter-wing connecting part 52' is positioned between the two thumb proximal knuckle connecting wings 621'; raised thumb hinged cylinders are arranged on two side faces of the thumb inter-wing connecting part 52'; the two thumb proximal knuckle connecting wing concentric holes are sleeved on the two thumb hinged cylinders respectively; two thumb base knuckle connecting wings 521' are arranged at the distal end of the thumb inter-wing connecting part 52'; and a thumb proximal finger joint locking pin 56' is jointly inserted and fixed on the thumb base knuckle connecting wing 521' and the thumb proximal knuckle connecting wing 621'. The adopted structures of the connecting wings and the hinged cylinders and the structure adopted by the proximal finger joint of a general prosthetic finger (not the thumb) have universality; the thumb proximal finger joint locking pin 56' is jointly inserted and fixed on the thumb base knuckle connecting wing 521' and the thumb proximal knuckle connecting wing 621' to lock a proximal finger joint of the thumb to ensure that the thumb base knuckle 5' and the thumb proximal knuckle 6' are relatively fixed, so that the structure is simple, the structural complexity of the prosthetic hand can be reduced, and the universality of the parts can be improved, thereby reducing the cost.

Similar to the previous prosthetic finger, according to the present embodiment, a sleeving mode is also adopted between the thumb proximal knuckle 6' and the thumb distal knuckle 7'; the thumb proximal knuckle 6' includes a thumb proximal knuckle raised head part 61' and a thumb proximal knuckle main body 62' thicker than the thumb proximal knuckle raised head part 61'; the thumb proximal knuckle connecting wing 621' is integrally connected to the proximal end of the thumb proximal knuckle main body 62'; and the thumb distal knuckle 7' is provided with the thumb distal knuckle sleeving part 71' which is sleeved on the thumb proximal knuckle raised head part 61' and butted against the thumb proximal knuckle main body 62'. Further, a thumb proximal knuckle raised head part threaded hole is formed in the thumb proximal knuckle raised head part 61', the axis of the thumb proximal knuckle raised head part threaded hole is perpendicular to the axis of the thumb proximal knuckle raised head part 61', a thumb distal knuckle screw mounting hole is formed in the thumb distal knuckle sleeving part 71' corresponding to the thumb proximal knuckle raised head part threaded hole, and a thumb distal knuckle mounting screw 72' is inserted in the thumb distal knuckle screw mounting hole and connected to the thumb proximal knuckle raised head part threaded hole. Here, fixing is carried out in conjunction with the thumb distal knuckle mounting screw 72', and the thumb proximal knuckle 6' and the thumb distal knuckle 7' are not easily detached from each other. Since the movement of the proximal knuckle of the thumb is locked, no transmission rope and tension spring are required. In the present embodiment, redundant tension spring accommodating grooves are formed in the thumb proximal knuckle raised head part 61' and the thumb proximal knuckle main body 62', and the tension spring is not connected to the thumb base knuckle 5' and the thumb proximal knuckle 6'.

In order to facilitate the assembly positioning between the thumb base knuckle 5' and the base joint rack 4, the thumb base knuckle main body 51' has a cavity for accommodating the thumb motor reducer assembly, a thumb fan-shaped flange is arranged on the upper outer wall of the thumb motor reducer assembly mounting part, a thumb slotted hole is formed in the thumb base knuckle main body 51' corresponding to the thumb fan-shaped flange, a part of the thumb base knuckle main body 51' is sleeved with a part of the thumb motor reducer assembly mounting part, and the thumb fan-shaped flange is positioned in the thumb slotted hole.

Similar to previous prosthetic finger, in order to enhance the connection reliability between the thumb worm gear and the thumb base joint rack and make the rotation more stable, the thumb worm gear includes a thumb rotating shaft connecting part; the thumb rotating shaft connecting part is provided with a thumb rotating shaft through hole; a thumb engaging part and a thumb worm gear fixing part are integrally connected to the thumb rotating shaft connecting part, and the thumb worm gear fixing part is fixed on the thumb mounting rack 1'; the thumb base joint rack includes a thumb motor reducer assembly mounting part, a thumb worm mounting part and two thumb rotating shaft through connection parts; the thumb motor reducer assembly mounting part and the thumb worm mounting part are connected into a whole through the two thumb rotating shaft through connection parts; a thumb open slot is formed between the two thumb rotating shaft through connection parts; the thumb worm gear is positioned in the thumb open slot; a thumb motor reducer assembly is mounted in the thumb motor reducer assembly mounting part; a thumb first bevel gear is fixed on a thumb output shaft journal of the thumb motor reducer assembly; a thumb worm is mounted in the thumb worm mounting part and is engaged with a thumb engaging part of the thumb worm gear; a thumb second bevel gear is fixed on a thumb input shaft journal of the thumb worm and is engaged with the thumb first bevel gear; thumb rotating shaft through connection concentric holes are formed in the two thumb rotating shaft through connection parts corresponding to the thumb rotating shaft through hole; and a thumb rotating shaft is inserted in the thumb rotating shaft through hole and the two thumb rotating shaft through connection concentric holes.

As the movement of a proximal finger joint of the thumb is locked, no transmission rope and tension spring are required. In the present embodiment, a redundant rope pulling part is integrally connected to the thumb rotating shaft connecting part, a redundant round hole with a gap is formed between the thumb engaging part and the rope pulling part, and the prosthetic thumb does not have a transmission rope. In this way, the thumb worm gear used by prosthetic thumb is actually the same worm gear as the worm gear 2 used by a general prosthetic finger, and the universality of the parts can be further increased.

In order to facilitate the assembly of the motor reducer assembly 401 in the base joint rack 4, a thumb motor reducer assembly mounting hole is formed in the thumb motor reducer assembly mounting part, the thumb motor reducer assembly includes a thumb motor, a thumb reducer is connected to the thumb motor, a thumb mounting neck is arranged on the thumb reducer, the diameter of the thumb mounting neck is smaller than that of the thumb reducer, a thumb output shaft journal extends out from the thumb mounting neck, and the thumb mounting neck is fixed in the thumb motor reducer assembly mounting hole.

In order to facilitate the assembly of the worm 404, a thumb worm main body accommodating cavity, a thumb sliding bearing mounting hole and a thumb worm journal accommodating hole are sequentially formed in the thumb worm mounting part in communication with one another; the diameter of the thumb sliding bearing mounting hole is smaller than that of the thumb worm main body accommodating cavity, and the diameter of the thumb worm journal accommodating hole is smaller than that of the thumb sliding bearing mounting hole; the end of the thumb worm main body accommodating cavity is opened, and a thumb elastic collar mounting groove is circumferentially arranged on the cavity wall of the thumb worm main body accommodating cavity; the thumb worm includes a thumb worm main body part, two ends of the thumb worm main body part are integrally connected with a thumb bearing mounting journal respectively, and one of the thumb bearing mounting journals is integrally connected with a thumb input shaft journal; the thumb worm main body part is positioned in the thumb worm main body accommodating cavity and is engaged with the thumb engaging part of the thumb worm gear; a thumb first sliding bearing is arranged in the thumb sliding bearing mounting hole, and a thumb second sliding bearing is arranged in the thumb worm main body accommodating cavity; the thumb worm main body part is positioned between the thumb first sliding bearing and the thumb second sliding bearing; one of the two thumb bearing mounting journals, which is connected with the thumb input shaft journal, is inserted in the thumb first sliding bearing, and the other one of the two thumb bearing mounting journals is inserted in the thumb second sliding bearing; a thumb elastic collar for hole is arranged in the thumb elastic collar mounting groove; and the thumb second sliding bearing is positioned between the thumb worm main body part and the thumb elastic collar for hole.

In order to facilitate the assembly of the two bevel gears, the thumb output shaft journal and the thumb input shaft journal are journals with D-shaped cross sections, each of the thumb first bevel gear and the thumb second bevel gear has a D-shaped center hole, the D-shaped center hole of the thumb first bevel gear is sleeved on the journal with the D-shaped cross section of the thumb output shaft journal, and the D-shaped center hole of the thumb second bevel gear is sleeved on the thumb input shaft journal.

In order to facilitate assembly of the thumb front supporting shaft 13, the thumb front supporting shaft 13 includes a head part and a screw part, the lead through hole 131 runs through the head part and the screw part, a nut mounting hole 111 is formed in the thumb front support 11, a thumb front supporting shaft nut 112 is arranged in the nut mounting hole 111, and the screw part is inserted in the thumb rotating rack 10 and the thumb front support 11 and connected to the thumb front supporting shaft nut 112.

In order to facilitate the assembly of the thumb back supporting shaft 14, the thumb back supporting shaft 14 includes a thumb back supporting shaft bolt and a thumb back supporting shaft nut, the thumb back supporting shaft nut is positioned in the thumb rotating rack open slot 101, and the thumb back supporting shaft bolt is inserted in the thumb back support 12 and the thumb rotating rack 10 and connected to the thumb back supporting shaft nut.

Figure 13:
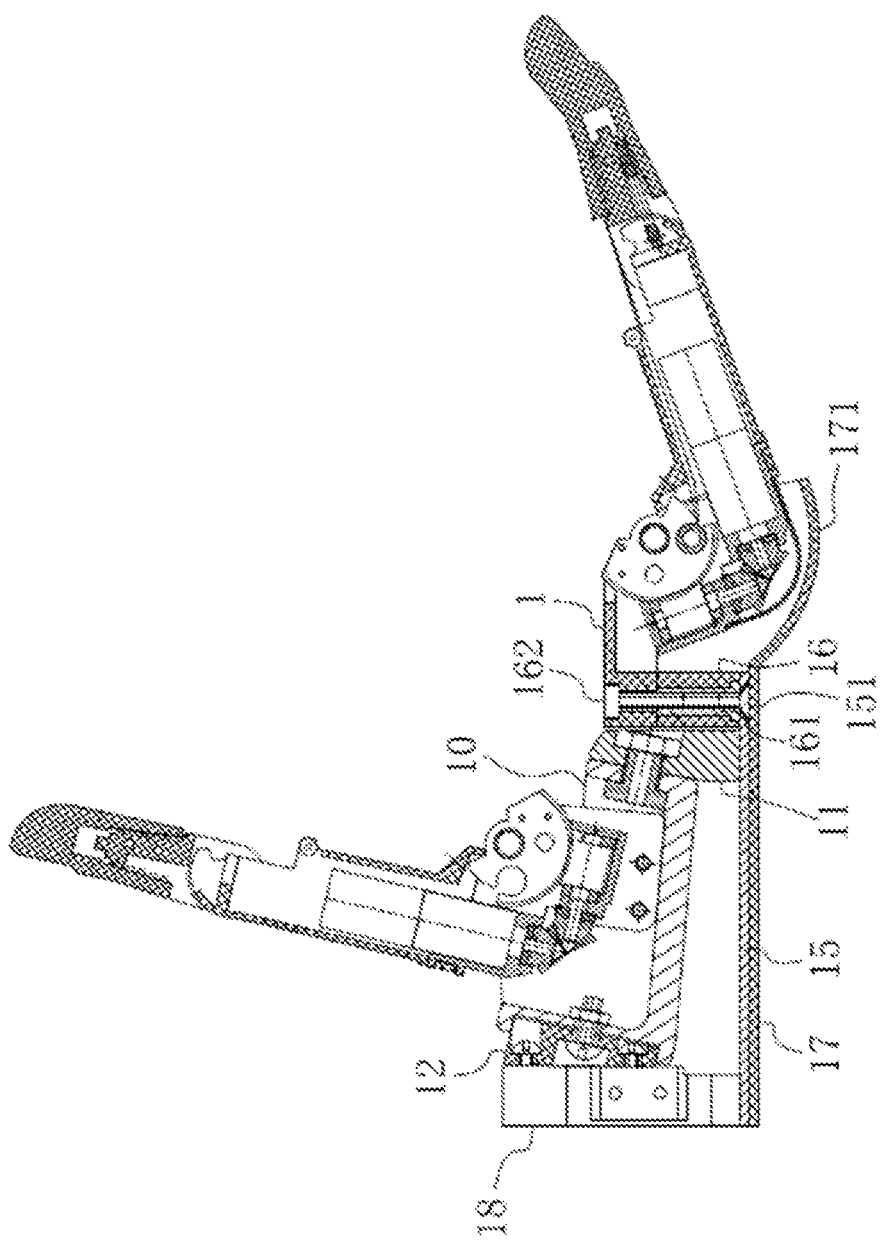
FIG. 13 is a schematic view of a structure of a prosthetic hand according to an embodiment of the present invention.

11. A Mounting Structure for the General Prosthetic Finger of the Prosthetic Hand The prosthetic hand provided by the embodiment of the present invention adopts the prosthetic finger mentioned above as a general prosthetic finger and the prosthetic thumb mentioned above as a prosthetic thumb, and the mounting structure for the general prosthetic finger of the prosthetic hand according to the embodiment of the present invention can be seen in FIG. 13 of the drawings in the specification. The mounting structure for the general prosthetic finger of the prosthetic hand, provided by the embodiment of the present invention, includes a prosthetic hand base plate 15, a finger connector 16 and a finger mounting rack 1 of the general prosthetic finger; a step-shaped hole (not shown) is formed in the finger connector 16; a step-shaped tension nut 161 is positioned in the step-shaped hole; the prosthetic hand base plate 15 is positioned at a side of a large-diameter end of the tension nut 161, and the finger mounting rack 1 is positioned at a side of a small-diameter end of the tension nut 161; a finger base plate connecting screw mounting hole (not shown) is formed in the prosthetic hand base plate 15 corresponding to internal threads of the tension nut 161, and a finger base plate connecting screw 151 is inserted in the finger base plate connecting screw mounting hole and connected to the internal threads of the tension nut 161; a finger connecting screw mounting hole (not shown) is formed in the finger mounting rack 1 corresponding to the internal threads of the tension nut 161, and a finger connecting screw 162 is inserted in the finger connecting screw mounting hole and connected to the internal threads of the tension nut 161; the axis of the finger connecting screw 162 is perpendicular to the pointing direction of the general prosthetic finger when the general prosthetic finger is in an unbent state.

According to the mounting structure for the general prosthetic finger of the prosthetic hand, provided by the embodiment of the present invention, the general prosthetic finger and the prosthetic hand base plate 15 are connected together by using the finger connector 16, the step-shaped tension nut 161, the finger connecting screw 162 and the finger base plate connecting screw 151, and the axis of the finger connecting screw 162 is perpendicular to the pointing direction of the general prosthetic finger, so that the connection is reliable and is not easy to loosen.

Since there are four general prosthetic fingers of the prosthetic hand, the numbers of step-shaped holes, the tension nuts 161, the finger connecting screws 162, and the finger base plate connecting screws 151 are four, in other words, four general prosthetic fingers are connected to the prosthetic hand base plate 15 simultaneously by using one finger connector 16.

In order to shield base finger joints of four general prosthetic fingers, a prosthetic hand back shell 17 is fixed on the prosthetic hand base plate 15, and is provided with general prosthetic finger base finger joint shield parts 171 which are positioned at the base finger joints of the four general prosthetic fingers, so that the general prosthetic fingers can be protected to some extent.

12. A Prosthetic Hand

The prosthetic hand provided by the embodiment of the present invention adopts the prosthetic finger mentioned above as a general prosthetic finger and the prosthetic thumb mentioned above as a prosthetic thumb, so that the prosthetic hand according to the embodiment of the present invention can be seen in FIGS. 1 to 13 of the drawings in the specification. Since the finger part of the prosthetic hand has been described in detail previously and the mounting of the general prosthetic finger has also been described, the description will not be repeated here. Here, only a brief description will be given on how the prosthetic thumb is mounted on the prosthetic hand base plate: the thumb front support 11 is fixed on the prosthetic hand base plate 15, the wrist connecting piece 18 is fixed on the prosthetic hand base plate 15, and the thumb back support 12 is fixed on the wrist connecting piece 18. The prosthetic hand provided by the present embodiment integrates the above-mentioned improvements in various aspects, the general prosthetic finger is reliable in connection, and the lead of the prosthetic thumb is protected, is not easy to break, and has higher reliability. Part of the structures of the prosthetic thumb and the prosthetic finger are universal, the cost can be reduced, and the parts are reliable in connection with one another and easy to assemble. The prosthetic hand according to the present embodiment has a self-locking function due to the adoption of the warm gear and a worm pair. The prosthetic thumb according to the present embodiment can be rotated in posture to have two states, namely an opposite palm state and a side palm state, and when the prosthetic thumb is reversed, a disabled person uses a healthy hand to carry it for rotary motion.

It should be noted that the prosthetic hand provided by the present embodiment integrates improvements in various aspects, but does not mean that they must be implemented together, and the improvements of various parts can be applied to existing prosthetic hands and fingers thereof individually. For example, the improvements of the connecting structure between the proximal knuckle and the base knuckle of the prosthetic finger and the connecting structure between the distal knuckle and the proximal knuckle of the prosthetic finger are not necessarily connected with whether the movement of the proximal knuckle of the prosthetic finger adopts cable transmission or not, and the movement of the proximal knuckle of the prosthetic finger can also adopt connecting rod transmission. In addition, the partial structure provided by the embodiment of the prosthetic finger can be applied not only to a general finger but also to a thumb.

What mentioned above are only specific implementations of the present invention, but the scope of protection of the present invention is not limited thereto, and any changes or substitutions that occur to those skilled in the art within the technical scope disclosed by the present invention are intended to be included within the scope of protection of the present invention. Therefore, the scope of protection of the present invention should be subject to the scope of protection of the claims.

What is claimed is:

1. A prosthetic finger, comprising a finger mounting rack, a worm gear, a rotating shaft, a base joint rack, a finger base knuckle, a finger proximal knuckle, a finger distal knuckle, a tension spring, and a transmission rope;

wherein the worm gear is fixed on the finger mounting rack, a round hole is provided on the worm gear, and a grommet is mounted in the round hole, wherein a hole edge of the round hole is clamped at a diameter reduced part of the grommet;

a motor reducer assembly is fixed in the base joint rack, a first bevel gear is fixed on an output shaft journal of the motor reducer assembly and the motor reducer assembly is structured to rotate the first bevel gear, a worm is mounted in the base joint rack, a second bevel gear is fixed on an input shaft journal of the worm, the second bevel gear is engaged with the first bevel gear, the base joint rack is provided with an open slot, the worm gear is positioned in the open slot and engaged with the worm, and the worm gear via a common penetration hole of the base joint rack and the worm gear;

the finger base knuckle has a cavity for accommodating the motor reducer assembly and is fixed on the base joint rack, the transmission rope runs through the finger base knuckle, and a proximal end of the transmission rope is connected to the grommet;

the finger proximal knuckle is rotatably connected to a distal end of the finger base knuckle, and the tension spring has two ends, one of the two ends is rotatably connected to the finger base knuckle and the other one of the two ends is rotatably connected to the finger proximal knuckle; and the finger proximal knuckle comprises a raised head part, a transmission rope connecting column is integrally arranged at a distal end of the raised head part, a distal end of the transmission rope is connected to the transmission rope connecting column, and a sleeving part is arranged on the finger distal knuckle and provided on the raised head part, and a part of the transmission rope is sandwiched between the sleeving part and the raised head part, wherein the rotating shaft is a hollow shaft, a finger tail cover is connected to the base joint rack, and the finger tail cover covers the first bevel gear and the second bevel gear, and the finger tail cover has two insertion posts which are inserted in the two ends of the hollow shaft respectively.

2. The prosthetic finger according to claim 1, wherein the finger base knuckle comprises a base knuckle main body, the transmission rope is positioned at a lower part in the base knuckle main body, a roller pin is fixed at a position corresponding to the transmission rope on a lower wall surface of the base knuckle main body, an axis of the roller pin is perpendicular to an axis of the base knuckle main body, a roller is provided on the roller pin, and a part of the roller extends into a space inside a wall surface of the base knuckle main body.

3. The prosthetic finger according to claim 1, wherein a distal end cylindrical pin is fixed on the finger proximal knuckle, a proximal end cylindrical pin is fixed on the finger proximal knuckle, an axis of the distal end cylindrical pin and an axis of the proximal end cylindrical pin are parallel to a rotation axis of the finger proximal knuckle, and one of the two ends of the tension spring is provided on one of the distal end cylindrical pin and the proximal end cylindrical pin and the other one of the two ends of the tension spring is provided on the other one of the distal end cylindrical pin and the proximal end cylindrical pin.

4. The prosthetic finger according to claim 1, wherein two proximal knuckle connecting wings are arranged at a proximal end of the finger proximal knuckle, and proximal knuckle connecting wing concentric holes are correspondingly formed in the two proximal knuckle connecting wings; the finger base knuckle comprises a base knuckle main body, an inter-wing connecting part is integrally connected at a distal end of the base knuckle main body, a width of the inter-wing connecting part is smaller than that of the base knuckle main body, and the inter-wing connecting part is positioned between the two proximal knuckle connecting wings; and convex hinged cylinders are arranged on two side faces of the inter-wing connecting part, and the two proximal knuckle connecting wing concentric holes are provided on the two hinged cylinders respectively.

5. The prosthetic finger according to claim 1, wherein both the output shaft journal and the input shaft journal are journals with D-shaped cross sections, each of the first bevel gear and the second bevel gear has a D-shaped center hole, the D-shaped center hole of the first bevel gear is provided on the journal with the D-shaped cross section of the output shaft journal, and the D-shaped center hole of the second bevel gear is sleeved on the input shaft journal.

6. The prosthetic finger according to claim 1, wherein the base joint rack comprises a motor reducer assembly mounting part, a worm mounting part, and two connection parts; the motor reducer assembly mounting part and the worm mounting part are connected into a whole through the two connection parts, and an open slot is formed between the two connection parts; the motor reducer assembly is fixed to the motor reducer assembly mounting part; the worm is mounted in the worm mounting part; the worm gear is provided with a rotating shaft through-hole; the two connection parts are provided with rotating shaft through connection concentric holes corresponding to the rotating shaft through-hole; and the rotating shaft runs through the rotating shaft through-hole and the two rotating shaft through connection concentric holes.

* * * * *